United States Patent [19]  
Fukuda et al.

[11] Patent Number: 5,039,789  
[45] Date of Patent: * Aug. 13, 1991

[54] A54145 CYCLIC PEPTIDES

[75] Inventors: David S. Fukuda, Brownsburg; Jon S. Mynderse, Indianapolis, both of Ind.

[73] Assignee: Eli Lilly and Company, Indianapolis, Ind.

[*] Notice: The portion of the term of this patent subsequent to Feb. 19, 2008 has been disclaimed.

[21] Appl. No.: 179,928

[22] Filed: Apr. 11, 1988

[51] Int. Cl.$^5$ .............................................. C07K 7/54
[52] U.S. Cl. ................................. 530/317; 530/323
[58] Field of Search ................................ 530/317, 323

[56] References Cited

U.S. PATENT DOCUMENTS

| | | | |
|---|---|---|---|
| 4,024,245 | 5/1977 | Hoehn et al. | 424/119 |
| 4,293,482 | 10/1981 | Abbott et al. | 260/112.5 R |
| 4,293,490 | 10/1981 | Abbott et al. | 260/112.5 K |
| 4,299,762 | 11/1981 | Abbott et al. | 260/112.5 R |
| 4,299,763 | 11/1981 | Abbott et al. | 260/112.5 R |
| 4,304,716 | 12/1981 | Abbott et al. | 260/112.5 R |
| 4,331,594 | 5/1982 | Hamill et al. | 424/115 |
| 4,482,487 | 11/1984 | Abbott et al. | 260/112.5 R |
| 4,524,135 | 6/1985 | Abbott et al. | 435/69 |
| 4,638,047 | 1/1987 | Szelke et al. | 530/332 |

Primary Examiner—John Doll  
Assistant Examiner—Christina chan  
Attorney, Agent, or Firm—Joseph A. Jones; Nancy J. Harrison; Leroy Whitaker

[57] ABSTRACT

A new group of cyclic peptides, the A54145 cyclic peptides, which have the general formula:

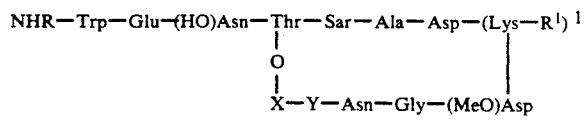

wherein:
R is selected from the group consisting of hydrogen, an amino-protecting group, 8-methylnonanoyl, 8-methyldecanoyl and n-decanoyl;
(Lys-R$^1$) represents —NH(CH$_2$)$_4$CH(NHR$^1$)CO—;
R$^1$ is hydrogen or an amino-protecting group;
X is Ile or Val: and
Y is Glu or 3-MG; provided that R$^1$ cannot be hydrogen when R is 8-methylnonanoyl, 8-methyldecanoyl or n-decanoyl;

and their salts are useful intermediates in the preparation of anitbacterial agents.

18 Claims, 4 Drawing Sheets

A54145 CYCLIC PEPTIDES

SUMMARY OF THE INVENTION

This invention relates to a new group of cyclic peptides, the A54145 cyclic peptides, which can be represented by formula 1:

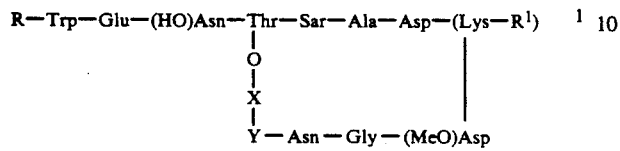

wherein:

R-Trp represents a group of formula:

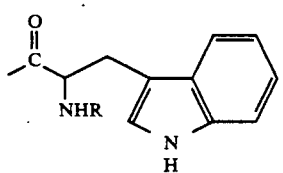

R is selected from the group consisting of hydrogen, an amino-protecting group, 8-methylnonanoyl, 8-methyldecanoyl and n-decanoyl;

(Lys-R$^1$) represents —NH(CH$_2$)$_4$CH(NHR$^1$)CO—;
R$^1$ is hydrogen or an amino-protecting group;
X is Ile or Val; and
Y is Glu or 3-MG;

provided that R$^1$ cannot be hydrogen when R is 8-methylnonanoyl, 8-methyldecanoyl or n-decanoyl.

The salts of the formula 1 compounds are also part of this invention.

The formula 1 compounds are useful intermediates in the preparation of semi-synthetic antibacterial agents and agents which improve growth performance in animals.

In other aspects, this invention relates to methods of preparing the formula 1 compounds wherein R is hydrogen by enzymatically deacylating either the corresponding natural A54145 components or the corresponding blocked A54145 components, using a deacylase produced by certain Actinoplanaceae, such as *Actinoplanes utahensis* NRRL 12052.

DESCRIPTION OF THE DRAWINGS

The $^1$H NMR spectra of the following A54145 nuclei (in D$_2$O) are presented in the accompanying drawings.

DETAILED DESCRIPTION OF THE INVENTION

Figure 1:
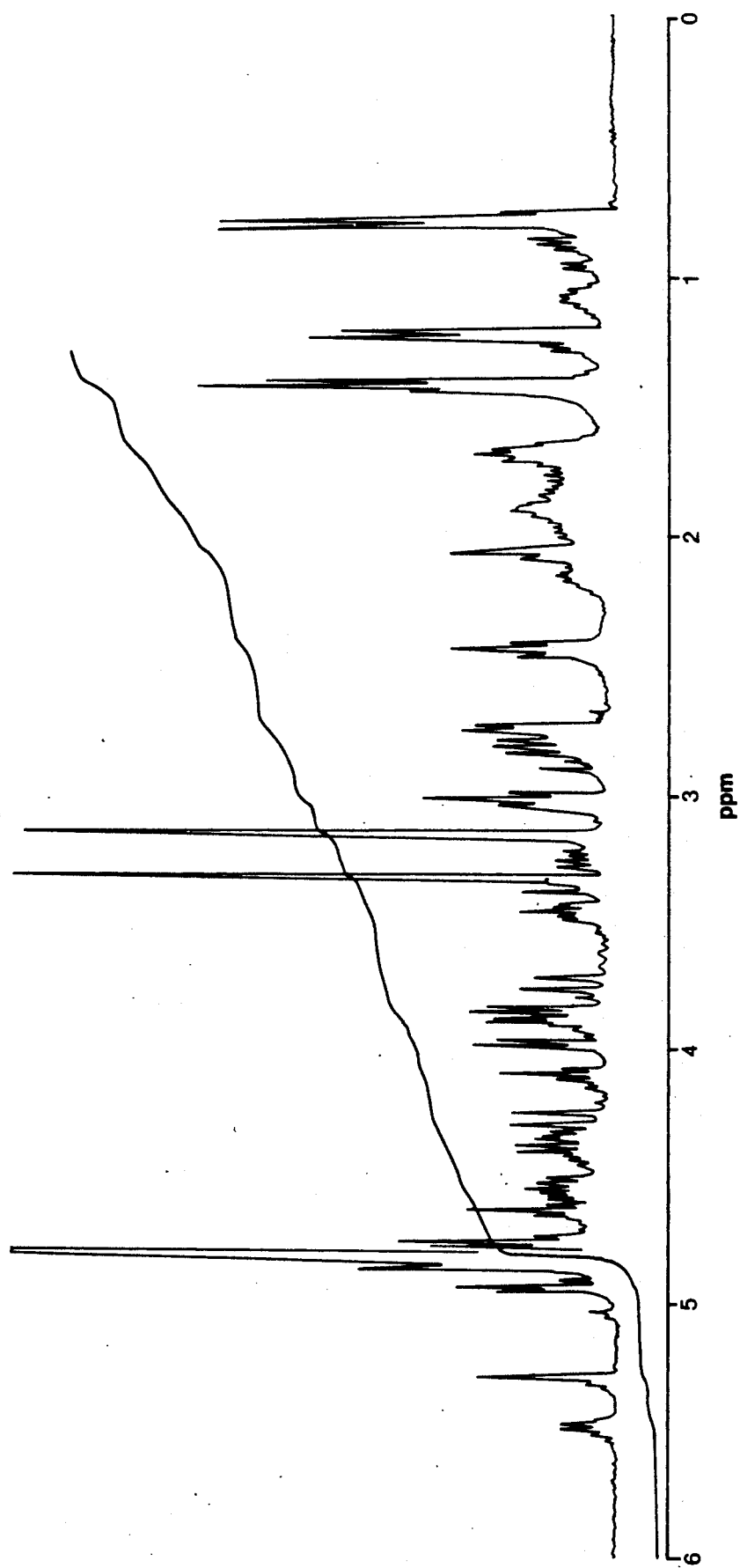
FIG. 1 - A54145A nucleus
FIG. 2 - A54145B nucleus
FIG. 3 - A54145F nucleus

In this specification the following abbreviations will be used:

| Abbreviation | Term |
|---|---|
| Ala: | Alanine |
| Asn: | Asparagine |
| (HO)Asn: | β-hydroxy-asparagine |
| Asp: | Aspartic acid |
| (MeO)Asp: | β-methoxy-aspartic acid |

| Abbreviation | Term |
|---|---|
| Glu: | Glutamic acid |
| Gly: | Glycine |
| Ile: | Isoleucine |
| Lys: | Lysine |
| Thr: | Threonine |
| Trp: | Tryptophan |
| Sar: | Sarcosine |
| Val: | Valine |
| 3-MG: | 3-Methylglutamic acid |
| HPLC: | High performance liquid chromatography |
| $^1$H NMR: | Proton nuclear magnetic resonance |
| TLC: | Thin-layer chromatography |
| IR: | Infrared |
| UV: | Ultraviolet |
| FABMS: | Fast-atom-bombardment mass spectrometry |

R$^a$-Trp represents a group of formula:

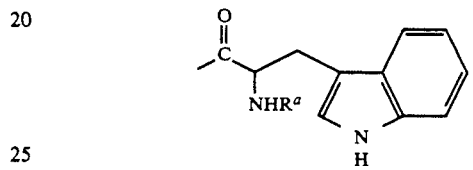

R$^b$-Trp represents a group of formula:

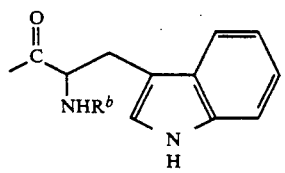

The A54145 antibiotics are acidic lipopeptide antibiotics. Each contains a cyclic peptide unit with a fatty acid side chain.

The A54145 components are believed to have general structure 2 and specific structures 2a–2h

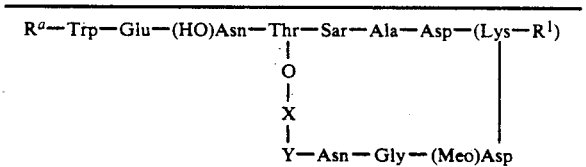

| Structure | Component | X | Y | R$^a$ |
|---|---|---|---|---|
| 2a | A | Ile | Glu | 8-methylnonanoyl |
| 2b | B | Ile | 3-MG | n-decanoyl |
| 2c | C | Val | 3-MG | 8-methyldecanoyl |
| 2d | D | Ile | Glu | " |
| 2e | E | Ile | 3-MG | " |
| 2f | F | Val | Glu | 8-methylnonanoyl |
| 2g | A$_1$ | Ile | Glu | n-decanoyl |
| 2h | B$_1$ | Ile | 3-MG | 8-methylnonanoyl |

We have discovered that the fatty acid side chains of the A54145 antibiotics can be removed enzymatically to give the cyclic peptide ("nucleus"). For convenience herein, this cyclic peptide will be called an A54145 nucleus. Thus far, four unique A54145 nuclei have been obtained. These nuclei have been designated the A54145A nucleus, the A54145B nucleus, the A54145C nucleus and the A54145F nucleus. Blocked A54145 components and blocked A54145 nuclei, which are useful intermediates to the A54145 nuclei, are also part of this invention. These compounds, which are called A54145 cyclic peptides, are represented by formula 1. Salts of the formula 1 peptides are also part of this invention.

A compound of formula 1 wherein R is other than hydrogen or an amino-protecting group and $R^1$ is an amino-protecting group is called a 1a compound or "blocked" A54145 component. A formula 1 compound wherein R and $R^1$ differ but are selected from hydrogen or an amino-protecting group is called a 1b compound or a "blocked nucleus".

A formula 1 compound wherein R and $R^1$ are both hydrogen is called a 1c compound or "nucleus".

The blocked components are useful intermediates to other peptides of formula 1, e.g. 1c compounds.

Likewise, the 1b compounds are useful intermediates to the 1c compounds.

Both the 1b and 1c compounds are useful in that they can be reacylated to provide new semisynthetic antibiotics. These new antibiotics are discussed in our co-pending application entitled A54145 DERIVATIVES, Ser. No. 07/179,929, filed this same day.

The term "amino-protecting group" refers to an art-recognized amino-protecting group which is compatible with the other functional groups in the A54145 molecule. Preferred amino-protecting groups are those which can be readily removed subsequently. Examples of suitable protecting groups can be found in "Protective Groups in Organic Synthesis" by Theodora W. Greene, John Wiley and Sons, N.Y. 1981, Chapter 7. Especially preferable amino-protecting groups are the tert-butoxycarbonyl (t-BOC) and benzyloxycarbonyl groups.

The methods of deacylating the A54145 antibiotics of this invention comprise exposing the antibiotic in an aqueous medium to an enzyme produced by a microorganism of the family Actinoplanaceae until substantial deacylation is accomplished. A preferred method comprises using an enzyme produced by the microorganism *Actinoplanes utahensis* NRRL 12052 to cleave the fatty acid side chain.

Deacylation is ordinarily accomplished by adding the appropriate A54145 component or blocked A54145 component to a growing culture of the *A. utahensis* strain and permitting the culture to incubate until deacylation is accomplished. The A54145 nucleus or blocked A54145 nucleus thereby obtained is separated from the fermentation broth by methods in the art.

A54145A Nucleus

A54145A nucleus is the compound of formula 1 wherein X=Ile, Y=Glu and R and $R^1$=H. It is the common cyclic peptide present in A54145 components A54145A, A54145D and A54145A$_1$. A blocked A54145A nucleus is a compound of formula 1 wherein X=Ile, Y=Glu, R=H and $R^1$=a protecting group.

A54145A nucleus is obtained by deacylating a peptide antibiotic selected from the group consisting of A54145A, A54145D, A54145A$_1$ and their salts. A blocked A54145A nucleus is obtained by deacylating a compound selected from blocked A54145A, blocked A54145D, blocked A54145A$_1$ and their salts.

Figure 4:
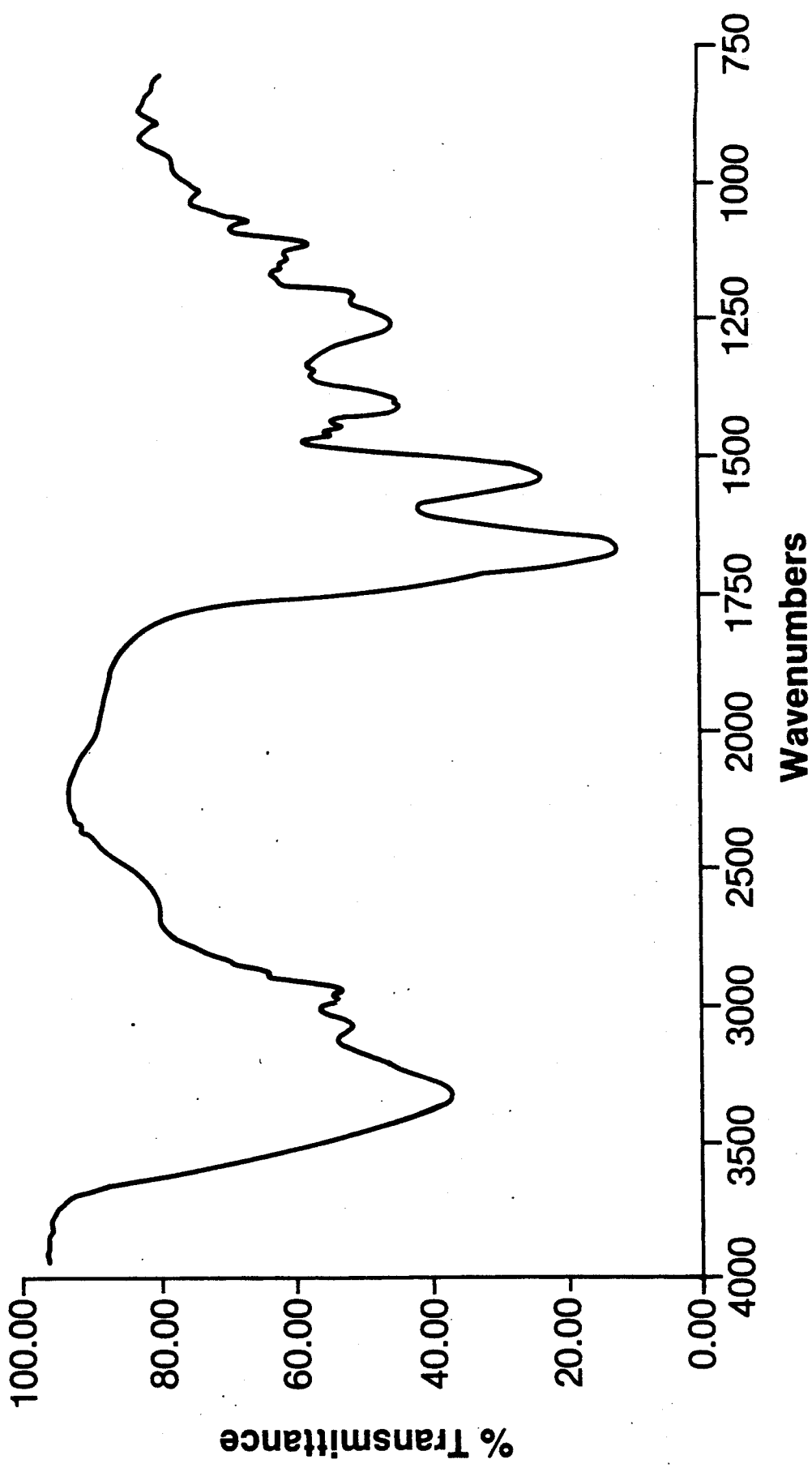
FIG. 4 is the IR spectrum of A54145A nucleus.

A54145A nucleus has the following characteristics:
Mol. wt. (FABMS): 1489
pKa (H$_2$O): 3.2, 4.3, 4.9, 5.6, 9.5
UV (EtOH): 217 nm ($\epsilon$ ~50,000), 279 ($\epsilon$ 4,100), 288 ($\epsilon$ 3,600)
IR (KBr): 3324, 3317, 3313, 3069, 1668, 1534, 1407, 1253, 1214 and 1200 cm$^{-1}$ (See FIG. 4)

Optical Rotation: $\alpha25°$ C./589D = $-4.93°$ (c, H$_2$O); $\alpha25°$ C./365 = $-23.65°$ (c, H$_2$O)
$^1$H NMR (360 MHz): See FIG. 1.
Analysis, Found: C, 45.36; H, 5.66; N, 12.74
Amino-Acid Analysis: Asp 722(2), Thr 321(1), Glu 734(2), Gly 368(1), Ala 362(1), Ile 339(1), Lys 362(1), Trp 286(1), Sar 377(1).

Amino-acid sequencing of the nucleus and FABMS of the A54145 components and A54145A nucleus suggest that A54145A nucleus has structure 3:

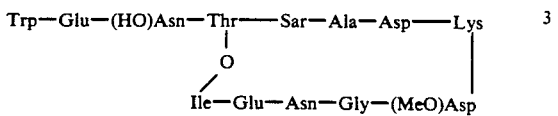

A54145B Nucleus

A54145B nucleus is the compound of formula 1 wherein X=Ile, Y=3-MG and R and $R^1$=H. It is the common cyclic peptide present in A54145 components A54145B, A54145B$_1$ and A54145E. A blocked A54145B nucleus is a formula 1 compound wherein X=Ile, Y=3-MG, R=H and $R^1$=an amino-protecting group.

A54145B nucleus is obtained by deacylating a peptide antibiotic selected from the group consisting of A54145B, A54145B$_1$, A54145E, and their salts. A blocked A54145B nucleus is obtained by deacylating a compound selected from blocked A54145B, blocked A54145B$_1$, blocked A54145E and their salts.

Figure 2:
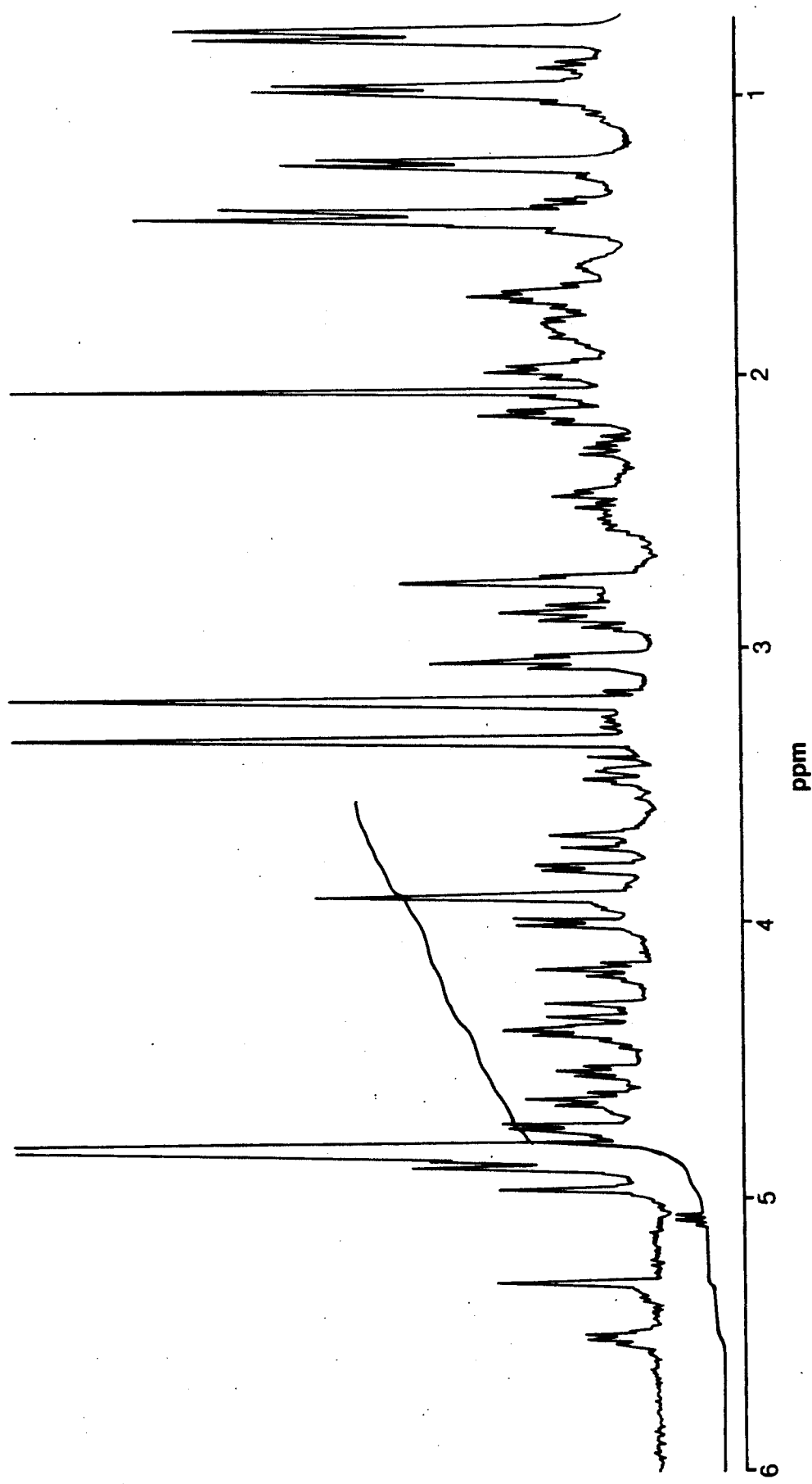

A54145B nucleus has the following characteristics:
Mol. wt. (FABMS): 1503
UV (EtOH): 218 nm ($\epsilon$ 31,193), 365 ($\epsilon$ 472), 279 ($\epsilon$ 5,308), 288 ($\epsilon$ 4,615)
IR (KBr): 3346, 3338, 3327, 3324, 3319, 3315, 3309, 1669, 1665 and 1540 cm$^{-1}$
Analysis, Found: C, 41.20; H, 5.58; N, 12.33
$^1$H NMR (270 MHz): See FIG. 2
Amino-Acid Analysis: Asp 1009(2), Thr 442(1), Glu 575(1), Gly 571(1), Ala 513(1), Ile 480(1), Lys 503(1), Trp 489(1), 3-MG 557(1).

Amino-acid sequencing and FABMS of the A54145 components and of A54145B nucleus suggest that A54145B nucleus has structure 4:

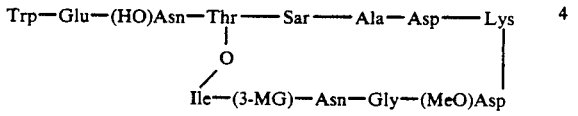

A54145C Nucleus

The compound of formula 1 wherein X=Val, Y=3-MG and R and $R^1$=H is the cyclic peptide present in A54145C and is, therefore, called A54145C nucleus. A54145C nucleus is obtained by deacylating A54145C or a salt of A54145C.

A blocked A54145C nucleus is a compound of formula 1 wherein X=Val, Y=3-MG, R=H and $R^1$=an amino-protecting group. A blocked A54145C nucleus is obtained by deacylating blocked A54145C or a salt of blocked A54145C.

A54145C nucleus has a molecular weight (FABMS) of 1489.

A comparison of its FABMS with that of A54145C suggests that A54145C nucleus has structure 5:

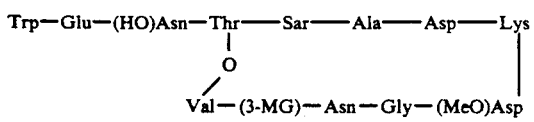

A54145F Nucleus

The compound of formula 1 wherein X=Val, Y=Glu and R and $R^1$=H is the cyclic peptide present in A54145F and is, therefore, called A54145F nucleus. A54145F nucleus is obtained by deacylating A54145F or a salt of A54145F.

A blocked A54145F nucleus is a compound of formula 1 wherein X=Val, Y=Glu, R=H and $R^1$=an amino-protecting group. A blocked A54145F nucleus is obtained by deacylating blocked A54145F or a salt of blocked A54145F.

Figure 3:
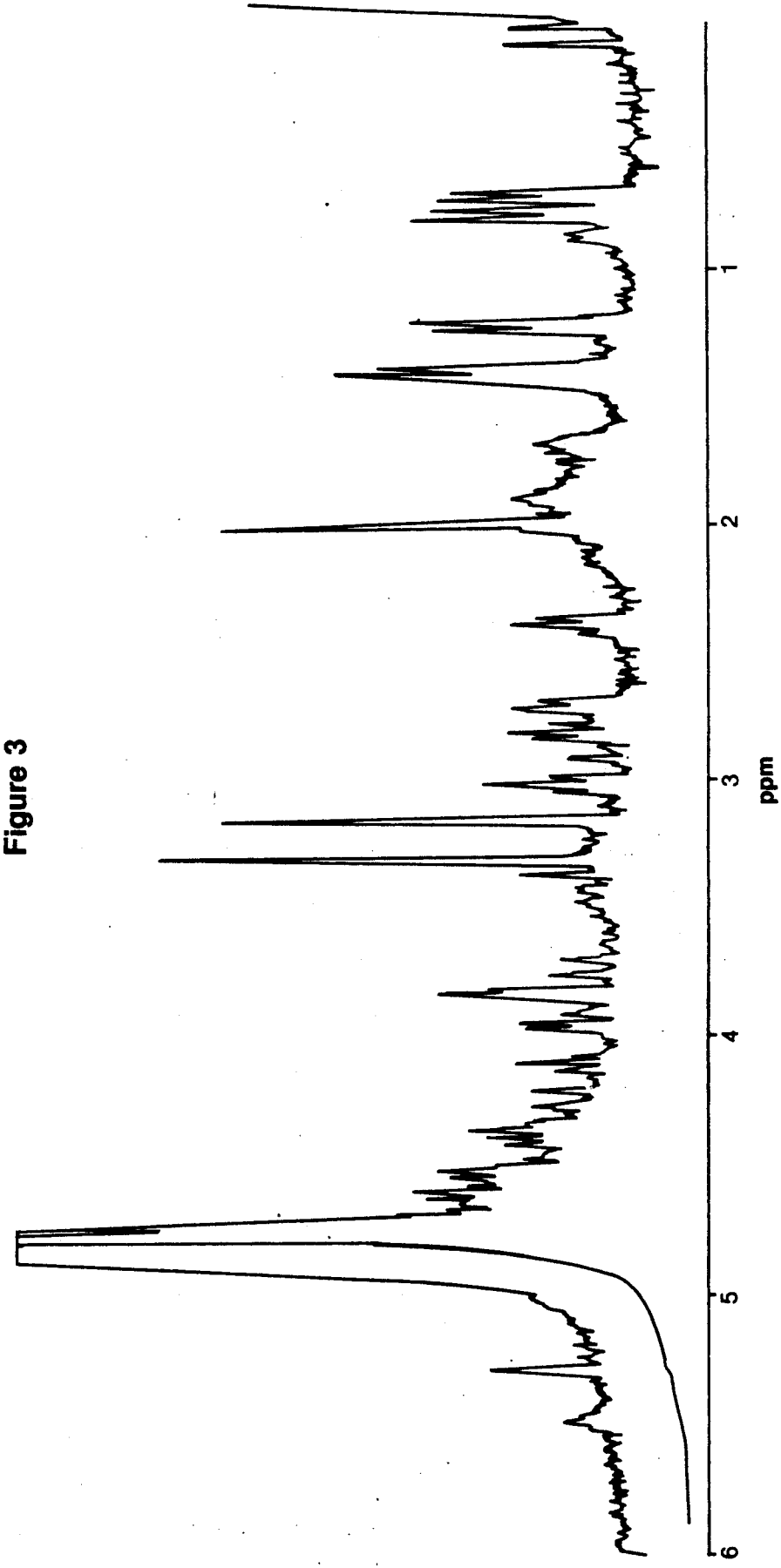

A54145F nucleus has the following characteristics:
Mol. Wt. (FABMS): 1475
UV (EtOH): 218 nm ($\epsilon$ 30,672), 278 ($\epsilon$ 4,547). 289 ($\epsilon$ 3,883)
IR (KBr): 3367, 3355, 3345, 3340, 3387, 1667 and 1542 $cm^{-1}$
$^1$H NMR (270 MHz): See FIG. 3
Analysis, Found: C, 37.87; H, 4.88; N, 11.29
Amino-Acid Analysis: Asp 962 (2), Thr 415 (1), Glu 974 (2), Gly 510 (1), Ala 486 (1), Val 459 (1), Lys 488 (1), Trp 393 (1).

A comparison of its FABMS with that of the A54145 components suggests that A54145F nucleus has structure 6:

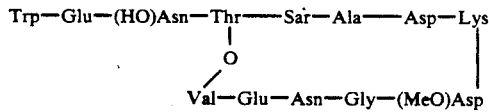

Thus, the four A54145 nuclei appear to have the common structure 7 and individual structures 7a–7d:

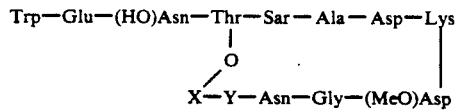

| Structure | A54145 Nucleus | X | Y |
|---|---|---|---|
| 7a | A | Ile | Glu |
| 7b | B | Ile | 3-MG |
| 7c | C | Val | 3-MG |
| 7d | F | Val | Glu |

The formula 1 compounds have both carboxyl and amino groups which can form salts such as alkali-metal, alkaline-earth metal, amine and acid addition salts. Partial, mixed and complete salts are, therefore, contemplated as part of this invention. Such salts are useful, for example, for separating and purifying the compounds.

Representative alkali-metal and alkaline-earth metal salts of the formula 1 compounds include the sodium, potassium, lithium, cesium, rubidium, barium, calcium and magnesium salts.

The alkali-metal and alkaline-earth-metal cationic salts of the formula 1 compounds are prepared according to procedures commonly used for the preparation of cationic salts. For example, the free acid form of the compound is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

Suitable amine salts of the formula 1 compounds include the ammonium and the primary, secondary, and tertiary $C_1$-$C_4$-alkylammonium and hydroxy-$C_2$-$C_4$-alkyl-ammonium salts. Illustrative amine salts include those formed by reaction of a formula 1 compound with ammonium hydroxide, methylamine, sec-butylamine, isopropylamine, diethylamine, di-isopropylamine, ethanolamine, triethylamine, 3-amino-1-propanol and the like.

The salts formed with organic amines can be prepared in a similar manner. For example, the gaseous or liquid amine can be added to a solution of the compound in a suitable solvent such as acetone; the solvent and excess amine can be removed by evaporation.

Representative and suitable acid-addition salts of the formula 1 compounds include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicyclic, methanesulfonic, benzenesulfonic, sorbic, picric, benzoic, cinnamic and like acids.

Pharmaceutically acceptable salts are especially useful. "Pharmaceutically-acceptable" salts are those in which the toxicity of the compound as a whole toward warm-blooded animals is not increased relative to the non-salt form. Pharmaceutically acceptable alkali-metal, alkaline-earth-metal and amine salts and acid-addition salts are particularly useful.

Preparation of the A54145 Cyclic Peptides

Scheme I outlines the general procedure for preparing the formula 1 compounds. In this Scheme, the following symbols are used:
[*]=remainder of the A54145 component
$N_T$=α-amino group of tryptophan
$N_L$=ε-amino group of lysine
$R_N$=acyl group of natural factor
B=amino-protecting group
Deacyl=a deacylation step
Block=acylation with an amino-protecting group
Deblock=removal of an amino-protecting group

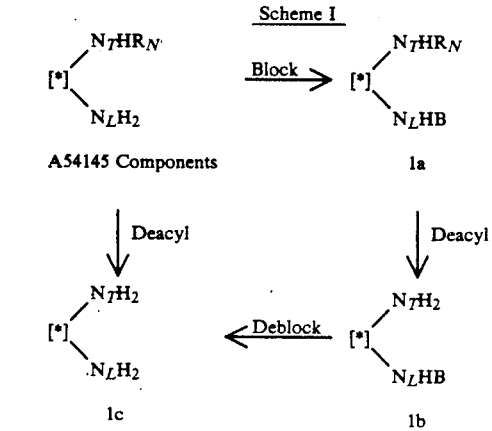

Scheme I

A. Preparing the Substrates

1. The A54145 Components

The cyclic peptides of formula 1 are prepared from the A54145 antibiotics. Antibiotic A54145, comprising major components A and B and minor components B, C, D, E, F and A, and its production by *Streptomyces fradiae* strains NRRL 18158, NRRL 18159 and NRRL 18160 are described by LaVerne D. Boeck, David S. Fukuda, Jon S. Mynderse, Marvin M. Hoehn, Ralph E. Kastner and Harold R. Papiska in their copending application entitled A54145 ANTIBIOTICS AND PROCESS FOR THEIR PRODUCTION, (Ser. No. 07/179,773), now U.S. Pat. No. 4,994,270 filed this same day. The A54145 antibiotics inhibit the growth of Gram-positive bacteria and promote growth in animals.

The A54145 antibiotics are produced by an A54145-producing strain of *Streptomyces fradiae* under submerged aerobic conditions in a suitable culture medium. Cultures of three A54145-producing *Streptomyces fradiae* strains have been deposited and made part of the stock culture collection of the Midwest Area Northern Regional Research Center, Agricultural Research Service, U.S. Department of Agriculture, 1815 North University Street, Peoria, Ill. 61604, from which they are available to the public under the accession numbers NRRL 18158, NRRL 18159 and NRRL 18160.

The culture medium used to grow the A54145-producing *Streptomyces fradiae* strains can be any one of a number of media. Preferred carbon sources are glucose, maltose, galactose, methyl oleate and peanut oil.

Preferred nitrogen sources are soybean grits, soybean flour or an enzymatic hydrolysate of soybeans.

Among the nutrient inorganic salts which may advantageously be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism.

Small amounts (i.e. 0.2 ml/L) of an antifoam agent such as polypropylene glycol may be added to large scale fermentation media if needed.

The A54145 antibiotics are produced by the *Streptomyces fradiae* strains when grown at temperatures between about 20° and about 35° C. A good temperature for A54145 production appears to be from about 25° C. to about 29° C.

As is customary in submerged aerobic culture processes, sterile air is blown into the vessel from the bottom while the medium is stirred with conventional turbine impellors. In a fully baffled 165-liter fermentor containing approximately 115 liters of broth, an aeration rate of 0.25 v/v/m with an agitation rate of 150–200 rpm is sufficient to maintain the level of dissolved oxygen at or above 30% of air saturation.

Production of antibiotic A54145 can be followed during the fermentation by testing samples of the broth for antibiotic activity against organisms known to be sensitive to the antibiotic. One assay organism useful in testing for antibiotic A54145 is *Bacillus subtilis*. The bioassay is conveniently performed by the agar-well plate test.

LaVerne D. Boeck has developed improved processes for preparing some of the A54145 components which he describes in his copending application entitled "PROCESSES FOR PREPARING A54145 COMPOUNDS", Ser. No. 07/179,930, now U.S. Pat. No. 4,977,083, filed herewith this even date.

One of these processes comprises feeding a $C_4$–$C_{18}$-alkanoic or alkenoic acid or alcohol, or an ester or salt thereof, to an A-54145-producing culture during its fermentation and recovering the A54145 components. This process provides significantly increased product yields of A54145 components.

In this process the alkyl portion of the alkanoic or alkenoic acid or alcohol (the substrate) used can be a straight or branched chain. The straight-chain acids or alcohols, or their esters or salts, are recommended because of availability and lower cost. An especially preferred substrate is n-decanoic acid and its esters and salts.

When using an alkanoic acid ester, the $C_1$–$C_4$-alkyl esters are preferred. In such an ester, the $C_1C_4$-alkyl group may also be straight or branched.

Representative suitable salts of alkanoic or alkenoic acids which may be used in this process include those formed from alkali metals and alkaline-earth metals such as sodium, potassium, lithium, cesium, rubidium, barium, calcium and magnesium. Suitable amine salts include the ammonium and the primary, secondary and tertiary $C_1$–$C_4$-alkyl-ammonium and hydroxy-$C_2$–$C_4$-alkyl-ammonium salts.

For this process it is preferable to add the substrate to the fermentation in the form of a sterile solution. For example, n-decanoic acid is a solid at room temperature, whereas its ethyl ester is a liquid. Thus, the ethyl ester is preferred because the acid must be dissolved in a compatible liquid, such as oleic acid or methyl oleate, for efficient feeding. Oleic acid is a particularly useful solvent for this purpose, although other solvents such as ethanol, ethyl acetate and $C_1$–$C_4$ esters of unsaturated fatty acids can be used. Those substrates which are suitably fluid at fermentation temperatures may be added directly and are, therefore, preferred.

The rate of addition of the substrate to the fermentation must be low enough to avoid producing a toxic effect on the fermentation, but high enough to increase the yield of the desired compound. Rates of addition of about 0.5 to about 4 mL of substrate per liter of fermentation broth per day can be used. A rate of from about 1.5 to about 3 mL of substrate per liter of fermentation broth per day is preferred.

The substrate is added to the growing A54145-producing culture during the production stage of the fermentation, beginning at from about 20 to about 26 hours and continuing until the fermentation is terminated. The substrate can be added by various methods. It is preferable, however, to add it by a method which best approaches a steady flow.

Another improved process for preparing A54145 compounds described in Boeck's application comprises feeding glucose at a rate from about 6 to about 9 grams/liter/day to an A54145-producing culture, starting from about 18 to about 24 hours after initiating the production stage and continuing throughout its fermentation. The improvement obtained by this process is illustrated in Table I, which compares the results obtained by standard methods with results obtained using this process.

TABLE I

Effect of Continuous Glucose Feed on A54145 Biosynthesis

| Glucose Level (%) | Glucose Addition Method | A54145 Yield (mcg/mL) |
|---|---|---|
| 4 | Included at time of medium make-up | 520 |
| 4 | Continuous feed from day 1 to day 8[a] | 1370 |

[a] Beginning 20 hours after initiating the production stage

As the results in Table I indicate, glucose feeding increases final A54145 yield by at least 150%.

In the continuous glucose feed process, the rate of addition of the glucose must be low enough to avoid toxic affects on the fermentation, but high enough to cause a significant increase in the yield of A54145 compound. A rate of about 6 to about 9 grams of glucose/liter of fermentation/day is recommended, but a rate of about 7.5 g/L/day is preferred for this process.

A third method for increasing product yields of A54145 components which Boeck describes comprises feeding an enzymatic soy digest to the fermentation at a rate of from about 2 to about 4 grams of soy digest/liter of fermentation broth/day to an A54145-producing culture, starting from about 90 to about 120 hours after initiating the production stage, and continuing throughout its fermentation.

Each of the Boeck processes can be carried out over a temperature range of from about 20° to about 34° C. Temperature affects the amount of total antibiotic produced and the type of nucleus and side chain produced. Thus, the temperature of the fermentation should be adjusted appropriately in order to obtain optimum yields of the desired product. Table II summarizes temperature effects on A54145 production which were observed in fermentation studies in which only the temperature was varied.

TABLE II

EFFECT OF TEMPERATURE ON A54145 NUCLEUS AND ACYL-CHAIN BIOSYNTHESIS IN A 165-L BIOREACTOR

| Temperature (°C.) | Total Antibiotic (mcg/mL) | Nuclei (%) | | | | Acyl Chains (%)[a] | | |
|---|---|---|---|---|---|---|---|---|
| | | A | B | C | F | $iC_{10}$ | $nC_{10}$ | $aC_{11}$ |
| 21 | 1015 | 60 | 31 | — | 9 | 79 | 15 | 6 |
| 25 | 1582 | 62 | 30 | — | 8 | 74 | 18 | 8 |
| 29 | 1623 | 39 | 51 | 3 | 6 | 64 | 21 | 14 |
| 31 | 1341 | 32 | 59 | 2 | 6 | 59 | 23 | 17 |
| 33 | 923 | 19 | 73 | 2 | 6 | 60 | 23 | 16 |

[a] $iC_{10}$ = 8-methylnonanoyl
$nC_{10}$ = n-decanoyl
$aC_{11}$ = 8-methyldecanoyl The A54145 components are recovered from the fermentation medium as a mixture, antibiotic A54145. Antibiotic A54145 can be obtained by filtering the fermentation broth, adjusting the pH of the filtrate to about pH 6, adsorbing the filtrate onto a resin such as HP-20 (Diaion) and eluting the antibiotic with a suitable solvent. A54145 can be further purified and the individual components can be separated by adsorption techniques. Individual A54145 components A, $A_1$, B, $B_1$, C, D, E and F have been isolated in this manner.

It is preferable, but not essential, to use purified A54145 component as the substrate. Because the purified substrate is soluble in water or in buffer, it can be handled more conveniently. Moreover, with purified substrate the deacylation proceeds more rapidly.

Since the substrate A54145 components have antibacterial activity, it is generally not necessary that the substrates be sterile, especially for short deacylation periods.

2. Blocked A54145 Components

The blocked A54145 components are prepared from the corresponding natural A54145 components using standing procedures for protecting amino groups. The blocked components are particularly useful for the subsequent preparation of derivatives.

B. Preparing the Enzyme

1. The Producing Microorganism

The enzyme which is useful for deacylating the A54145 components and blocked A54145 components is produced by certain microorganisms of the family Actinoplanaceae, preferably the microorganism *Actinoplanes utahensis* NRRL 12052.

The enzyme may be the same enzyme which has been used to deacylate penicillins (see Walter J. Kleinschmidt, Walter E. Wright, Frederick W. Kavanagh, and William M. Stark in U.S. Pat. No. 3,150,059, issued Sept. 22, 1964), the A-30912-type antibiotics (see Bernard J. Abbott and David S. Fukuda in U.S. Pat. Nos. 4,293,482; 4,293,490; 4,299,762; 4,299,763 and 4,304,716, all issued in 1981) or the A-21978C antibiotics (see Bernard J. Abbott, Manuel Debono and David S. Fukuda in U.S. Pat. No. 4,524,135, issued June 18, 1985).

Although a preferred method of cultivating *A. utahensis* NRRL 12052 to produce this enzyme is described in Example 1, it will be recognized by those skilled in the art that other methods may be used.

The Actinoplanageae are a family of microorganisms of the order Actinomycetales. Of the genera in the family Actinoplanaceae, the genus Actinoplanes is a preferred source of the enzyme which is useful for this invention. Within the genus Actinoplanes, the species *Actinoplanes utahensis* is an especially preferred source.

Cultures of representative useful species are available to the public from the Northern Regional Research Center, address supra, under the following accession numbers:

| | |
|---|---|
| *Actinoplanes utahensis* | NRRL 12052 |
| *Actinoplanes missouriensis* | NRRL 12053 |
| *Actinoplanes* sp. | NRRL 8122 |
| *Actinoplanes* sp. | NRRL 12065 |
| *Streptosporangium roseum* var. *hollandensis* | NRRL 12064 |

*Actinoplanes utahensis* NRRL 12052 was derived from a parent culture which was deposited with the American Type Culture Collection (ATCC), 12301 Parklawn Drive, Rockville, Md. 20852 (*A. utahensis* ATCC 14539). The *A. utahensis* ATCC 14539 culture may also be used as a source of the enzyme.

*Actinoplanes missouriensis* NRRL 12053 was derived from a culture which was deposited with ATCC (*A. missouriensis* ATCC 14538) and which may be another source of the enzyme.

The effectiveness of any given strain of microorganism within the family Actinoplanaceae for carrying out the deacylation of this invention is determined by the following procedure. A suitable growth medium is inoculated with the microorganism. The culture is incubated at about 30° C. for two or three days on a rotary shaker. One of the substrate antibiotics is then added to the culture. The pH of the fermentation medium is maintained at about pH 7. The culture is monitored for activity using a *Micrococcus luteus* assay. This procedure is described infra in Section D. Loss of antibiotic activity is an indication that the microorganism produces the requisite enzyme for deacylation. This must be verified, however, using one of the following methods: 1) analysis by HPLC for presence of the intact nucleus; or 2) re-acylation with an appropriate side chain (e.g. n-decanoyl or n-undecanoyl) to restore activity.

2. Conditions for Enzyme Production

Production of the enzyme occurs under conditions satisfactory for growth of the Actinoplanaceae, i.e., a temperature between about 25° and about 30° C. and a pH of between about 5.0 and about 8.0, with agitation and aeration. The culture medium should contain a) an assimilable carbon source such as sucrose, glucose, glycerol, or the like; b) a nitrogen source such as peptone, urea, ammonium sulfate, or the like; c) a phosphate source such as a soluble phosphate salt; and d) inorganic salts found generally to be effective in promoting the growth of microorganisms. An effective amount of the enzyme is generally obtained in from about 40 to about 60 hours after the beginning of the growth cycle and persists for some time after the effective growth has been reached. The amount of enzyme produced varies from species to species of the organism and in response to different growth conditions.

As will be apparent to those in the field, the microorganisms, such as *Actinoplanes utahensis* NRRL 12052, which produce the enzyme are subject to variation. For example, spontaneous and induced mutants of these strains may be obtained by natural selection or by treatment with various known mutagens such as ultraviolet rays, X rays, high-frequency waves, ionizing radiation and chemicals. All spontaneous and induced mutants which are obtained from the Actinoplanaceae and which produce the enzyme may be used in this invention.

C. Deacylating the Substrate

The substrate used as the starting material is preferably added to the culture of Actinoplanaceae after the culture has been incubated for at least about 48 hours. The concentration of substrate in the conversion medium can vary widely. For maximum use of the enzyme and for substantially complete deacylation within a 6-hour period, however, the concentration of substrate will generally range from about 0.5 to about 1 mg/mL. Lower concentrations can be used, but may not make maximum use of the enzyme; higher concentrations can also be used, but the substrate may not be completely deacylated unless the fermentation time is extended.

Conversion of the substrate antibiotic to the corresponding A54145 nucleus proceeds best when the pH of the fermentation medium is maintained in the range of from about 7 to about 7.2. Below pH 7, deacylation proceeds slowly; as pH values move above pH 7.2, the nucleus which is formed is increasingly subject to alkaline hydrolysis. In stirred fermentors the pH may be controlled by sensor controllers. Where this is impractical, such as in flask fermentors, pH can be controlled by adding 0.1 molar phosphate buffer to the medium prior to adding the substrate.

After adding the substrate, the culture should be incubated for about 3-6 hours or longer. The purity of the substrate will affect the rate of deacylation. For example, substrate having a purity of greater than 50 percent is deacylated at a rate of about 0.3–0.5 mg/mL of antibiotic per hour. When substrates of lower purity are used, the deacylation proceeds at a somewhat slower rate. Multiple substrate feedings may be made.

The deacylation can be carried out over a broad temperature range, e.g. from about 20° to about 37° C. It is preferable, however, to carry out the deacylation at a temperature of about 30° C. for optimum deacylation and stability of substrate and nucleus.

D. Monitoring the Deacylation

The A54145 antibiotics are antibacterial agents which are active against sensitive Gram-positive organisms such as *Staphylococcus aureus, Bacillus subtilis* and *Micrococcus luteus*. For this reason, an assay using a sensitive Gram-positive organism is preferable for determining quantities of substrate present. The A54145 nuclei which form are water soluble, but are biologically inactive. Reduction in biological activity is, therefore, a quick, presumptive test for deacylation.

The amount of nucleus formed can be quantitated by HPLC analysis, using the system herein described.

E. Resting Cells

An alternate method of deacylation involves removing the Actinoplanaceae cells from the culture medium, resuspending the cells in a buffer solution, and carrying out the deacylation as described in Section B. When this method is used, the enzymatically active mycelia can be re-used. For example, *A. utahensis* NRRL 12052 mycelia retain deacylase activity after storage for one month or longer under refrigeration (4°–8° C.) or in the frozen state (−20° C.). A preferred buffer solution is 0.1 molar phosphate buffer.

F. Immobilized Enzymes

Yet another method of carrying out the deacylation is, to immobilize the enzyme by methods known in the art (See, for example, "Biomedical Applications of Immobilized Enzymes and Proteins", Thomas Ming Swi Chang, Ed., Plenum Press, New York, 1977, Vol. 1). The immobilized enzyme can then be used in a column (or other suitable type of reactor) to effect the deacylation.

In addition, the microorganism itself can be immobilized and used to catalyze the deacylation reaction.

Utility of the A54145 Cyclic Peptides

The formula 1 compounds are useful intermediates in the preparation of semi-synthetic antibacterial compounds. These compounds are described in our copending application Docket No. X-6848(Ser. No. 07/179,929), discussed supra.

One group of these compounds can be represented by formula 8:

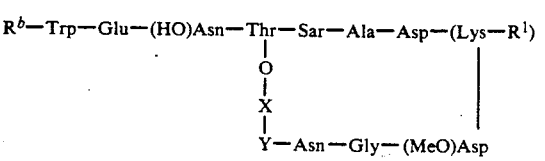

wherein:
$R^b$ is $C_8$-$C_{18}$-alkanoyl or $C_8$-$C_{18}$-alkenoyl;

(Lys-R¹), R¹, X and Y are as defined, supra; provided that: 1) when R¹=H, X=Ile and Y=Glu or 3-MG, $R^b$ cannot be 8-methylnonanoyl, 8-methyldecanoyl or n-decanoyl; 2) when R¹=H, X=Val and Y=3-MG, $R^b$ cannot be 8-methyldecanoyl; and 3) when R¹=H, X=Val and Y=Glu, $R^b$ cannot be 8-methylnonanoyl; and salts of these compounds.

The formula 8 compounds are prepared by acylating a formula 1 compound which is blocked at the ε-amino group of lysine with the desired alkanoyl or alkenoyl side chain, using methods conventional in the art for forming an amide bond. The acylation is accomplished, in general, by reacting the selected compound with an activated derivative of the alkanoic acid or alkenoic acid corresponding to the desired acyl side chain group ($R^b$). The term "activated derivative" means a derivative which renders the carboxyl function of the acylating agent reactive to coupling with the primary amino group to form the amide bond which links the acyl side chain to the nucelus. Suitable activated derivatives, their methods of preparation, and their methods of use as acylating agents for a primary amine will be recognized by those skilled in the art.

Preferred activated derivatives are: (a) an acid halide (e.g. an acid chloride), (b) an acid anhydride (e.g., an alkoxyformic acid anhydride) or (c) an activated ester (e.g. a 2,4,5,-trichlorophenyl ester). Other methods for activating the carboxyl function include reacting the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

The formula 8 compounds have shown in vivo antimicrobial activity against experimentally-induced infections in mice, e.g. infections with *Streptococcus pyogenes* or *Staphylococcus aureus*.

The formula 8 compounds also improve growth performance in animals. The compounds are especially effective growth promoters in fowl, such as chickens and turkeys, but should also be effective in other animals such as swine.

The formula 8 compounds are typically effective in improving growth performance in animals when administered with feed at a rate of from about 0.05 to about 100 grams of compound per ton of feed (0.055 to 110 ppm). A preferred rate is from about 0.05 to about 50 g/ton, and an especially preferred rate is from about 1 to about 20 g/ton. The compounds can be administered to animals orally or parenterally. The most practical way to administer the compound is by formulation into the feed supply.

The following examples are provided to illustrate this invention. In these examples the following numbers will be used to represent specific solvent systems:

| No. | System | Ratio |
|---|---|---|
| 1 | Pyridine/HOAc/H₂O | 1:1:98 |
| 2 | Pyridine/HOAc/H₂O/CH₃CN | 1:1:88:10 |
| 2a | " | 1:1:87:11 |
| 2b | " | 1:1:86:12 |
| 2c | " | 1:1:83:15 |
| 2d | " | 1:1:82:16 |
| 2e | " | 1:1:78:20 |
| 2f | " | 1:1:73:25 |
| 2g | " | 1:1:70.5:27.5 |
| 2h | " | 1:1:68:30 |
| 2i | " | 1:1:67:31 |
| 2j | " | 1:1:66:32 |
| 2k | " | 1:1:65:33 |
| 2m | " | 1:1:63:35 |
| 3a | Pyridine/HOAc/H₂O/CH₃CN/MeOH | 1:1:70:18:10 |
| 3b | " | 1:1:68:20:10 |
| 3c | " | 1:1:63:25:10 |
| 3d | " | 1:1:61:27:10 |
| 3e | " | 1:1:58:30:10 |
| 3f | " | 1:1:56:32:10 |
| 3g | " | 1:1:53:35:10 |
| 3h | " | 1:1:68:25:5 |
| 3i | " | 1:1:73:15:10 |
| 3j | " | 1:1:60.5:25:12.5 |
| 3k | " | 1:1:71:20:7 |
| 4 | CH₃CN/H₂O | 1:1 |
| 4a | " | 15:85 |
| 5 | CH₃OH/H₂O | 1:1 |

Separation of the individual antibiotic A54145 components can be followed by TLC or HPLC. One convenient analytical HPLC system is:

Analytical HPLC System for A54145 Components

Column: 4.6-×250-mm Zorbax C8 (Dupont)
Mobile Phase: acetonitrile/water containing 0.2% tri ethylamine and adjusted to pH 3 with phosphoric acid (35:65)
Detection: UV at 223 nm
Flow Rate: 2 mL/min A54145 components A-F have the following approximate retention times in this system:

| A54145 Factor | Retention Time (min) |
|---|---|
| A | 12.1 |
| A₁ | 13.1 |
| B | 14.9 |
| B₁ | 13.7 |
| C | 17.0 |
| D | 19.6 |
| E | 22.4 |
| F | 9.4 |

Formation and purification of the A54145 nuclei can be monitored by analytical HPLC, using the following system:

Analytical HPLC System for A54145 Nuclei

Column: 4.6-×250 mm Zorbax ODS (Dupont, 5μ)
Detection: UV at 223 nm
Flow Rate: Usually 2 mL/min
Solvent System: CH₃CN/0.04M aq. NH₄OAc (9:91)

PREPARATION 1

Producing Antibiotic A54145 with *Streptomyces fradiae* A54145.1

A. Shake-flask Fermentation of A54145.1

The culture *Streptomyces fradiae* NRRL 18158, either as a lyophilized pellet or as a suspension maintained in liquid nitrogen, is used to inoculate 50 mL of a vegetative medium having the following composition:

| Vegetative Medium I | |
|---|---|
| Ingredient | Amount (g/L) |
| Glucose | 15.0 |
| Potato dextrin | 20.0 |
| Soybean grits | 15.0 |
| Corn steep liquor | 10.0 |

-continued

| Vegetative Medium I | |
|---|---|
| Ingredient | Amount (g/L) |
| Yeast extract | 1.0 |
| CaCO$_3$ | 5.0 |
| Tap water | q.s. 1 liter |
| (Adjust the pH of the medium from ~6.1 to ~6.5 with NaOH before sterilizing; post-sterilization pH ~7) | |

The inoculated first-stage medium is incubated in a 250-mL Erlenmeyer flask at 30° C. for about 48 hours on a shaker orbiting in a two-inch (5.08 cm) circle at 250 rpm.

This incubated first-stage medium (1 mL) is used to inoculate 50 mL of a production medium having the following composition:

| Production Medium I | |
|---|---|
| Ingredient | Amount (g/L) |
| Glucose | 45 |
| Soybean grits | 35 |
| Blackstrap molasses | 3 |
| CaCO$_3$ | 2.5 |
| Tap water | q.s. 1 liter |
| (Presterilization pH ~6.9; post-sterilization pH ~6.8) | |

The inoculated production medium is incubated in a 250-mL wide-mouth Erlenmeyer flask at 25° C. for 6 to 7 days on a shaker orbiting in a two-inch circle at 250 rpm.

B. Tank Fermentation of A54145.1

In order to provide a larger volume of inoculum, 10 mL of incubated vegetative medium, prepared as described in Section A, is used to inoculate 400 mL of a second-stage growth medium having the same composition as that of the first-stage vegetative medium. This second-stage vegetative medium is incubated in a two-liter wide-mouth Erlenmeyer flask for about 24 hours at 30° C. on a shaker orbiting in a two-inch circle at 250 rpm.

Incubated second-stage vegetative medium (800 mL) thus prepared is used to inoculate 115 liters of sterile production medium, prepared as described in Section A, except that 0.2 g/L of a silicone antifoam such as Sag-471 (Union Carbide) is added. The inoculated production medium is allowed to ferment in a 165-liter stirred fermentation tank for 6 to 7 days at a temperature of 25° C. Low airflow (0.25 v/v/m) and low rpm (200–300) in the stirred vessel maintain a dissolved oxygen level above 30% of air saturation. The pH is not allowed to rise above 7.5.

PREPARATION 2

Producing Antibiotic A54145 with *Streptomyces fradiae* A54145.2

A. Shake-flask Fermentation of A54145.2

Shake-flask fermentation is carried out as in Preparation 1, Section A, with the following exceptions:
1) the culture is *Streptomyces fradiae* NRRL 18159;
2) the vegetative medium has the following composition:

| Vegetative Medium II | |
|---|---|
| Ingredient | Amount (g/L) |
| Glucose | 10 |
| Potato starch | 30 |
| Soybean flour | 20 |
| Defatted cottonseed flour | 20 |
| CaCO$_3$ | 2 |
| Tap water | 1 liter |

3) the vegtative medium is incubated at 25° C.; and
4) the production medium has the following composition:

| Production Medium II | |
|---|---|
| Ingredient | Amount (g/L) |
| Glucose | 25.0 |
| Soybean grits | 18.75 |
| Blackstrap molasses | 3.75 |
| Casein | 1.25 |
| CaCO$_3$ | 3.125 |
| Sodium acetate | 8.0 |
| Tap water | q.s. to 1 L |
| (Pre-sterilization pH ~6.9; post-sterilization pH ~6.8) | |

B. Tank Fermentation of A54145.2

Incubated vegetative medium prepared as described in Section A is used, and the procedures of Preparation 1, Section B, are followed with these following exceptions:
1) the amount of incubated vegetative medium used to inoculate the second-stage growth medium is 8 mL;
2) the amount of second-stage medium used to inoculate the production medium is 2L;
3) the air flow is 0.125 v/v/m; and
4) the pH is allowed to rise above 7.5.

PREPARATION 3

Producing Antibiotic A54145 with *Streptomyces fradiae* A54145.3

The procedures of Preparation 2, Section B, are followed except that 1) the culture used is *Streptomyces fradiae* NRRL 18160, 2) dissolved oxygen is controlled at 40% of air saturation, 3) pH is controlled at 7.0 and 4) the production medium has the following composition;

| Production Medium III | |
|---|---|
| Ingredient | Amount (g/L) |
| Soybean flour | 20.0 |
| Glucose | 5.0 |
| Blackstrap molasses | 2.5 |
| Fe(SO$_4$).(NH$_4$)$_2$SO$_4$.6H$_2$O | 0.6 |
| Silicon defoamer | 0.2 |
| Polypropylene glycol (M.W. 2000) | 0.1 |
| Tap water | q.s. to 1 liter |

PREPARATION 4

Isolating Antibiotic A54145

Procedure A: Whole fermentation broth from two 100-L tanks (217L), prepared as described in Preparation 2, was filtered through a filter press with the aid of 3% filter aid (Hyflo Super-Cel, Manville Products, Lompoc Calif.). The filtrate (185L) was adjusted to pH 6.4, using 5N HCl. Diaion HP-20 resin (20L) was added to the filtrate. The initial effluent (85L) and a water wash (60L) were discarded. The resin was then eluted as follows:

| Eluate | Solvent No. | Amount |
| --- | --- | --- |
| 1 | 4a | 40 L |
| 2 | 4 | 30 L |
| 3 | 4 | 30 L |

Eluate 1 was discarded.

Eluates 2 and 3 were combined and chromatographed on 2L of IRA-68(OAc−) (2.5"×32"). The initial effluent (60L), a wash with Solvent No. 4 (10L) and an eluate with 0.1N HOAc:CH$_3$CN (1:1, 10L) were discarded. The column was then eluted with 14L of 1.0N HOAc:CH$_3$CN (1:1). This fraction was concentrated under vacuum and lyophilized to give 101.1 g of antibiotic A54145.

Procedure B: Whole fermentation broth from a large tank (4600L), prepared as described in Preparation 2, was adjusted to pH 6.5 with HCl and filtered through a filter press with the aid of 4% Celite 545 to give 4600L of filtrate having a pH of 6.3.

The filtrate was absorbed batch-wise onto Diaion HP-20 resin (200 L), adjusted to pH 6.0 and maintained at this pH while stirring for 2 hours. The mixture was filtered, and the filtrate was discarded.

The saturated HP-20 resin was transferred to a small tank with a welded membrane. The resin was washed first with water (800L), agitating for 35 minutes, and then with Solvent No. 4a (400L), agitating for 3 minutes. These washes were discarded. The resin was then eluted twice with Solvent No. 4 (600L), agitating for 35 minutes.

The eluates were combined (1200L) and chromatographed on an IRA-68 resin column (100L), equilibrated in Solvent No. 4 and washed with this solvent (500L). The column was then eluted with CH$_3$CN:0.2N HOAc (1:1), discarding the first fractions (300L) and combining, concentrating and lyophilizing subsequent fractions (750L) to give 3.65 kg of antibiotic A54145.

PREPARATION 5

Separating A54145B, A54145C, A54145D and A54145E

Antibiotic A54145 (60 g), obtained as described in Preparation 4, was subjected to preparative HPLC using a Chromatospac 100, 4-L Quantum LP-1/C18 silica-gel column (3"×39"). The antibiotic was dissolved in Solvent No. 1 and added to the column. Elution was monitored by UV at 280 nm.

Fractions were combined based on analytical HPLC as described supra, but detecting at 289 and 223 nm and collecting 500-mL fractions at a flow rate of 100 mL/min. The column was eluted as follows:

| Solvent | Fractions |
| --- | --- |
| 1 | 1-8 |
| 3b | 9-29 |
| 3c | 30-73 |
| 3d | 74-161 |
| 4 | 8-L strip |

On the basis of the analytical HPLC results, fractions 114-161 were combined to give a total of 8.5 g of antibiotic A54145 enriched with components B, C, D and E. This material was rechromatographed on a Chromatospac column, repeating the previous conditions, but detecting at 223 nm and using the following solvents:

| Solvent | Fractions |
| --- | --- |
| 1 | 1-8 |
| 3c | 9-41 |
| 3f | 42-60 |
| 3h | 61-83 |
| 4 | 8-L strip |

From this column, fractions 76-78 gave 1.75 g of A54145B-enriched material, fractions 79-83 gave 1.02 g of A54145C-enriched material, and the strip fraction gave 0.8 g of A54145D-enriched material.

PREPARATION 6

Separating A54145 Enriched with A54145A, A54145C and A54145F

A54145 (60 g), obtained as described in Preparation 4, Procedure B, was chromatographed as in Preparation 5, but using the following solvents:

| Solvent | Fractions |
| --- | --- |
| 1 | 1-8 |
| 3c | 9-102 |
| 4 | 103-122 |

Fractions were combined on the basis of analytical HPLC to give 2.54 g of A54145F-enriched material, 5.1 g of A54145A-enriched material and 10.56 g of A54145C-enriched material.

PREPARATION 7

Isolating A54145A

A54145A-enriched material (1 g), obtained as described in Preparation 6, was purified, using the following preparative HPLC system: two 1"×12" stainless steel columns packed with Zorbax ODS (12μ) in series.

Detection: UV at 280 nm

Flow Rate: 9 mL/minute

The material was dissolved in Solvent No. 1 for injection onto the column. The column was eluted as follows:

| Solvent | Fractions[a] |
| --- | --- |
| 1 | 1-18 |
| 3a | 19-145 |
| 4 | 146-165 |

[a]Fraction volume = 18 mL

Fractions containing A54145A (fractions 86-96) were combined, concentrated under vacuum and lyophilized to give 212 mg of purified A54145A.

Characteristics of A54145A

Mol. Wt.: 1643

Mol. Formula: $C_{72}H_{109}N_{17}O_{27}$

High Resolution FABMS(M+H): Found: 1644.7778, Calcd. for $C_{72}H_{110}N_{17}O_{27}$: 1644.7757

UV (EtOH) $\lambda_{max}$: 219 nm ($\epsilon$ 35,000), 280 ($\epsilon$ 5,250), shoulder 288 ($\epsilon$ 4,600)

IR (KBr): essentially the same as that of A54145B, infra

Optical Rotation: [α]25° C./589 No Rotation (CH$_3$OH); [α]25° C./365 −14.0° (c 0.1, CH$_3$OH)

Amino-acid Analysis: Asp 973(2), Thr 441(1), Glu 1056(2), Gly 528(1), Ala 549(1), Ile 469(1), Trp 465(1)

PREPARATION 8

Isolating A54145B

The A54145B-enriched A54145 material obtained in Preparation 5 (500 mg) was chromatographed using the procedure of Preparation 7. The column was eluted as follows:

| Solvent No. | Fractions[a] |
|---|---|
| 1 | 1–16 |
| 3g | 17–95 |
| 5 | 96–115 |

[a]Fraction volume = 18 mL

Fractions containing A54145B (fractions 64–70) were combined, concentrated under vacuum and lyophilized to give 330 mg of purified A54145B.

Characteristics of A54145B

Mol. Wt.: 1657

Mol. Formula: $C_{73}H_{111}N_{17}O_{27}$

High Resolution FABMS(M+H): Found: 1658.7954, Calcd. for $C_{73}H_{112}N_{17}O_{27}$: 1658.7914

UV (EtOH) $\lambda_{max}$: 220 nm ($\epsilon$ 41,854), 281 ($\epsilon$ 5,613), 289 ($\epsilon$ 5,084)

IR (KBr): ranging from 3335 to 3313; 2930, 1660, 1531, 1407, 1255 cm$^{-1}$

Optical Rotation: [α]25° C./589 = −8.55° (c 0.47 H$_2$O); [α]25° C./365 = −36.32° (c 0.47, H$_2$O)

Amino-acid Analysis: Asp 1039(2), Thr 466(1), Glu 564(1), Gly 528(1), Ala 525(1), Ile 491(1), Lys 541(1), Trp 491(1), 3-MG 512(1).

PREPARATION 9

Isolating A54145C

A54145C-enriched material (11.76 g), obtained as described in Preparations 5 and 6, was purified using the following preparative HPLC system:

Column: 2"-×60-cm stainless steel
Packing: Quantum LP-1/C18 silica gel (20 mμ)
Detection: UV at 280 nm
Flow Rate: 18 mL/min The material was dissolved in pyridine/HOAc/H$_2$O (1:1:98, 37 mL) for application to the column. The column was eluted as follows:

| Solvent No. | Fractions[a] |
|---|---|
| 1 | 1–10 |
| 3e | 11–160 |
| 3h | 161–550 |
| 4 | 551–582 |

[a]Fraction volume = 18 mL

Fractions containing A54145C were combined (fractions 320–331, 817.8 mg). This material (800 mg) was further purified by HPLC using a 1"×20" stainless-steel column packed with Quantum LP-1/C18 (20 mμ) silica gel column, detecting as in Preparation 7, and applying the material in pyridine/HOAc/H$_2$O (1:1:98, 15 mL).

The column was eluted at a flow rate of 8 mL/min as follows:

| Solvent No. | Fractions[a] |
|---|---|
| 1 | 1–18 |
| 3f | 19–69 |
| 3g | 70–114 |
| 5 | 115–137 |

[a]Fraction volume = 16 mL

Fractions containing A54145C (fractions 84–86 and 92–98) were combined, concentrated and lyophilized to give 350 mg of C-enriched material.

This process was repeated with some variation in the solvents used, i.e., varying the amount of CH$_3$CN in the solvent and sometimes eliminating methanol in the solvent mixture, to give an additional 27.6 mg of purified A54145C.

Characteristics of A54145C

Mol. wt.: 1657

Mol. Formula: $C_{73}H_{111}N_{17}O_{27}$

High Resolution FABMS(M+H): Found: 1658.7905, Calcd. for $C_{73}H_{112}N_{17}O_{27}$: 1658.7914

UV (EtOH) $\lambda_{max}$: 219 nm ($\epsilon$ 29,500), 281 ($\epsilon$ 4,200), 288 ($\epsilon$ 3,600)

IR (KBr): essentially the same as that of A54145B, supra;

Amino-acid Analysis: Asp 934(2), Thr 414(1), Glu 594(1), Gly 501(1), Ala 459(1), Val 359(1), Lys 451(1), 3-MG 487(1), Trp 308(1).

PREPARATION 10

Isolating A54145D

A54145D-enriched material (750 mg), obtained as described in Preparation 5 was purified using the preparative HPLC system described in Preparation 7, except that only one column was used. The material was applied to the column in 25 mL of the solvent, and the column was eluted at a flow rate of 7.5 mL/min as follows:

| Solvent No. | Fractions[a] |
|---|---|
| 1 | 1–6 |
| 3g | 7–89 |
| 2k | 90–101 |
| 4 | 102–115 |

[a]Fraction volume = 15 mL

Fractions containing A54145D (19–22) were combined, concentrated and lyophilized to give 219 mg of material further enriched with A54145D.

This material was purified by a second HPLC column, using the same conditions except that 5% methanol was added to solvent 4 and solvent 2 k was eliminated.

The fractions from this column containing A54145D (fractions 72–74) were combined, concentrated and lyophilized to give 70 mg of purified A54145D.

Characteristics of A54145D

Mol. Wt.: 1657

Mol. Formula: $C_{73}H_{111}N_{17}O_{27}$

High Resolution FABMS(M+H): Found: 1658.7913, Calcd. for $C_{73}H_{112}N_{17}O_{27}$: 1658.7914

UV (EtOH) $\lambda_{max}$: 219 nm ($\epsilon$ 37,500), 280 ($\epsilon$ 5,040), 289 ($\epsilon$ 4,500)

IR (KBr): essentially the same as that of A54145B, supra;

Amino-acid Analysis: Asp 1011(2), Thr 427(1), Glu 967(2), Gly 515(1), Ala 487(1), Ile 434(1), Lys 543(1), Trp 577(1)

PREPARATION 11

Isolating A54145E

A54145E-enriched material (1.0 g), obtained as described in Preparation 5, was purified using a preparative HPLC system as in Preparation 9, but using a 1"×20" column. The material was applied in 15 mL of solvent, and the column was eluted at a flow rate of 9 mL/min as follows:

| Solvent No. | Fractions[a] |
| --- | --- |
| 1 | 1–19 |
| 2h | 20–118 |
| 2j | 119–215 |
| 4 | 216–225 |

[a]Fraction volume = 18 mL

Fractions containing A54145E (fractions 147–160) were combined, concentrated and lyophilized to give 49.7 mg of material further enriched with A54145E.

This material was purified using two 9.4- ×250-mm Zorbax ODS (5µ) columns in series, detecting by UV at 280 nm. The material was applied to the column in 3 mL of solvent 1, and the column was eluted at a flow rate of 3.25 mL/min as follows:

| Solvent No. | Fractions[a] |
| --- | --- |
| 1 | 1–12 |
| 2i | 13–180 |
| 4 | 181–193 |

[a]Fraction volume = 6.5 mL

Fractions containing A54145E (fractions 143–160) were combined, concentrated and lyophilized to give 16.07 mg of purified A54145E.

Characteristics of A54145E

Mol. Wt.: 1671

Mol. Formula: $C_{74}H_{113}N_{17}O_{27}$

High Resolution FABMS(M+H): Found: 1672.8065, Calcd. for $C_{74}H_{114}N_{17}O_{27}$: 1672.8069

UV (EtOH) $\lambda_{max}$: 221 nm ($\epsilon$ 29,714), 278 ($\epsilon$ 4577) 289 (4044)

IR (KBr): essentially the same as that of A54145B, supra

Amino-acid Analysis: Asp 826(2), Thr 367(1), Glu 494(1), Gly 437(1), Ala 422(1), Ile 378(1), Lys 410(1), Trp 387(1), 3-MG 437(1)

PREPARATION 12

Isolating A54145F

A54145F-enriched material (800 mg), obtained as described in Preparation 6, was purified using an HPLC system as in Preparation 9, but with a 1"×20" column. The material was applied to the column in 10 mL of solvent 1, and the column was eluted at a flow rate of 8 mL/min as follows:

| Solvent No. | Fractions[a] |
| --- | --- |
| 1 | 1–10 |
| 2f | 11–60 |
| 2g | 61–99 |
| 2k | 100–134 |
| 4 | 135–150 |

[a]Fraction volume = 16 mL

Fractions containing A54145F (fractions 120–128) were combined, concentrated and lyophilized to give 366.2 mg of purified A54145F.

Characteristics of A54145F

Mol. Wt.: 1629

Mol. Formula: $C_{71}H_{107}N_{17}O_{27}$

High Resolution FABMS(M+H): Found: 1630.7634, Calcd. for $C_{71}H_{108}N_{17}O_{27}$: 1630.7601

UV (EtOH) $\lambda_{max}$: 219 nm ($\epsilon$ 36,750), 280 ($\epsilon$ 5,100), 288 ($\epsilon$ 4,450)

IR (KBr): essentially the same as that of A54145B, supra

Optical Rotation: $[\alpha]25°$ C./589 = $-3.0°$ (c 1.0, $H_2O$); $[\alpha]25°$ C./365 = $-6.0°$ (c 1.0, $H_2O$)

Amino-acid Analysis: Asp 959(2), Thr 428(1), Glu 965(2), Gly 494(1), Ala 487(1), Val 363(1), Lys 492(1), Trp 452(1).

PREPARATION 13

Isolating A54145A$_1$

Procedure A:

A54145A$_1$-enriched material was obtained using the following procedure: Whole broth (103L), prepared as described in Preparation 2, was treated as described in Preparation 4 Procedure A except that instead of the IRA-68(OAc$^-$) column, the combined eluates were graphed over a 40-×780-mm BioRex 5 (Cl$^-$) column, using gradient elution with a 0.1N–1.0N NaCl solvent system and collecting 100-mL fractions.

Fractions containing A54145 were combined and desalted over a 40-×400-mm HP-20 column, again collecting 100-mL fractions. Fractions containing A54145 were combined and lyophilized to give 12.08 g of antibiotic A54145.

A portion of this antibiotic A54145 (2 g) is subjected to preparative HPLC using a Waters PrepPak 500 (C18) column, using a linear gradient of water to $H_2O/CH_3CN$ (1:1) containing 1% $NH_4H_2PO_4$. Fractions containing A54145A$_1$ are collected and desalted over an HP-20 column, eluting with Solvent 4.

This step is repeated twice, and the A$_1$-enriched material is combined (937 mg).

The A$_1$-enriched material is chromatographed over two 1"×12" Zorbax ODS columns in series as described in Preparation 7. Fractions containing A54145A$_1$ are eluted with Solvent 2j, combined, concentrated and lyophilized to give crude A54145A$_1$ (109 mg).

This material is further purified by repeating this step to give more purified A54145A$_1$ (69.29 mg).

The material is even further purified by repeating this procedure three times, using Solvents 3j, 3h and 3k, respectively. The product obtained is desalted over HP-20 to give purified A54145A$_1$ (12.21 mg).

Procedure B:

Whole fermentation broth (160L) is prepared as described in Preparation 17. With this procedure, the fermentation volume increases with time; therefore, beginning at 138 hours, 10-L aliquots are removed at intervals and frozen. By harvest (287 hours), a total of 50L is removed and frozen. The frozen broth is added back to the fermentation at harvest. The whole broth is filtered with a filter aid or separated using a centrifuge. A portion of the filtrate (55L) is worked up using the procedure of Preparation 14. Fractions containing A54145A$_1$ are eluted with solvent 4, concentrated and freeze-dried. Following this procedure gave 111.3 g of A54145A$_1$-enriched material.

This material is chromagraphed over a 1"×16" Zorbax C8 (12μ) column. The column is eluted with solvent 2h. Following this procedure gave 374 mg of further A54145A$_1$-enriched material, which contained approximately 46% A54145A$_1$, 19% A54145B$_1$, 14% A54145A, 13% A54145B and 8% of an unidentified material (HPLC analysis).

Preparative HPLC using appropriate solvents is carried out on the further purified material to obtain A54145A$_1$ in pure form.

Characteristics of A54145A$_1$

Mol. Wt.: 1643
Mol. Formula: $C_{72}H_{109}N_{17}O_{27}$
High Resolution FABMS(M+H): Found: 1644.7691, Calcd. for $C_{72}H_{110}N_{17}O_{27}$: 1644.7757
UV (EtOH) $\lambda_{max}$: 220 nm ($\epsilon$ 41,623), 281 ($\epsilon$, 5,750), 289 ($\epsilon$ 4,950)
Optical Rotation: $[\alpha]25°$ C./589 −10.4° (c 0.69, CH$_3$OH)
Amino-acid Analysis: Asp 1209(2), Thr 554(1), Glu 1209(2), Gly 636(1), Ala 617(1), Ile 576(1), Lys 604(1), Trp 514(1)

PREPARATION 14

Isolating A54145B$_1$

Whole fermentation broth (100L), prepared as described in Preparation 3, was worked up as described in Preparation 4, Procedure A, except that chromatography on IRA-68 was omitted. The material was eluted with solvent 4a, concentrated and freeze-dried to give 248.2 g of crude antibiotic A54145.

A portion of this material (60 g) was chromatographed on a 2"×60-cm LP-1/C18 silica gel column.
Detection: UV at 254 and 280 mm.
Flow Rate: 25 mL/minute/fraction.
The column was eluted as follows:

| Solvent No. | Fractions |
|---|---|
| 1 | 1–138 |
| 2f | 139–411 |
| 2h | 412–560 |
| 2m | 561–976 |
| 4 | 977–1000 |

Fractions containing A54145B and A54145B$_1$ were pooled and concentrated as follows:

| Pool | Fraction | Weight (g) |
|---|---|---|
| 1 | 951–1000 | 1.10 |
| 2 | 635–667 | 4.62 |
| 3 | 685–719 | 3.95 |

The A54145B and A54145B$_1$-enriched fractions (Pools 2–3) were further purified over two 1"×12" Amicon C18 columns in series.
Detection: UV at 280 mm.
Flow Rate: 20 mL/1.6 minute/fraction.
The columns were eluted with pyridine/HOAc/H$_2$O/CH$_3$CN (0.1/0.1/67.3/32.5). Fractions containing A54145B were combined to give 554 mg of A54145B, and fractions containing A54145B$_1$ were combined to give 207 mg of purified A54145B$_1$.

Other A54145B-enriched fractions (Pool 1) were also purified in this manner to give an additional 394.5 mg of A54145B.

Characteristics of A54145B$_1$

Mol. Wt.: 1657
Mol. Formula: $C_{73}H_{111}N_{17}O_{27}$
High Resolution FABMS(M+H): Found: 1658.7911 Calcd. for $C_{73}H_{112}N_{17}O_{27}$: 1658.7914
UV (EtOH) $\lambda_{max}$: 221 nm ($\epsilon$ 39,100), 282 ($\epsilon$, 5,500). 290 ($\epsilon$ 4,740)
IR (KBr): essentially the same as that of A54145B, supra.
Amino-acid Analysis: Asp 935(2), Thr 422(1), Glu 556(1), Gly 480(1), Ala 434(1), Ile 438(1), Lys 467(1), Trp 440(1), 3-MG 426(1);

PREPARATION 15

Effect of Lipid Precursors, Media and Feeding Enzymatic Soy Digest on A54145 Production A54145 fermentations were carried out as in Preparation 3, but using the following three production media, with and without lipid feeding:

| Medium A | |
|---|---|
| Ingredient | Amount (g/L) |
| Glucose | 25.0 |
| Soybean grits | 15.0 |
| Blackstrap molasses | 3.0 |
| Acid-hydrolyzed casein | 1.0 |
| CaCO$_3$ | 2.5 |
| Tap water | q.s. 1 liter |
| (Pre-sterilization pH ~7.0; post-sterilization pH ~7.1) | |

| Medium B | |
|---|---|
| Ingredient | Amount (g/L) |
| Soybean flour | 20.0 |
| Glucose | 5.0 |
| Blackstrap molasses | 2.5 |
| Fe(SO$_4$).(NH$_4$)$_2$SO$_4$.6H$_2$O | 0.6 |
| Silicon defoamer | 0.2 |
| Polypropylene glycol (M.W. 2000) | 0.1 |
| Potato dextrin | 30.0 |
| Tap water | q.s. to 1 liter |

| Medium C | |
|---|---|
| Ingredient | Amount (g/L) |
| Soybean flour | 20.0 |
| Glucose | 5.0 |
| Blackstrap molasses | 2.5 |
| Fe(SO$_4$).(NH$_4$)$_2$SO$_4$.6H$_2$O | 0.6 |
| Silicon defoamer | 0.2 |
| Polypropylene glycol (M.W. 2000) | 0.1 |

-continued

| Medium C | |
|---|---|
| Ingredient | Amount (g/L) |
| Tap water | q.s. to 1 liter |

Medium D

Medium C with an enzymatic-soy-digest (Hy Soy, Sheffield Products, Norwich N.Y.) feeding.

Table III summarizes the results of these studies.

TABLE III

EFFECT OF LIPID PRECURSORS AND MEDIA ON YIELDS AND FACTOR SIDE CHAINS OF A54145 IN A 165-L BIOREACTOR

| Medium | Lipid Precursor[a] | Total Antibiotic (mcg/mL) | Factor Side Chains (%)[b] | | |
|---|---|---|---|---|---|
| | | | $iC_{10}$ | $nC_{10}$ | $aC_{11}$ |
| A | — | 97 | 68 | 20 | 12 |
| A | $nC_{10}$ | 179 | 20 | 79 | 1 |
| B | — | 570 | 70 | 17 | 13 |
| B | $nC_{10}$ | 1046 | 7 | 91 | 2 |
| C | — | 1100 | 76 | 14 | 10 |
| C | $nC_{10}/C_{18:1}$ | 2316 | 19 | 74 | 7 |
| D | $nC_{10}/C_{18:1}$ | 3570 | 21 | 71 | 8 |

[a]$nC_{10}$ = ethyl caprate
$nC_{10}/C_{18:1}$ = n-decanoic acid in methyl oleate (1:1)
[b]$iC_{10}$ = 8-methylnonanoyl
$nC_{10}$ = n-decanoyl
$aC_{11}$ = 8-methyldecanoyl

PREPARATION 16

Effect of Amino-Acid Enrichment on A54145 Production

A54145 fermentations were carried out as in Preparation 2, Section A, but using the culture used in Preparation 3 and the following production medium:

| Ingredient | Amount (g/L) |
|---|---|
| Glucose | 30.00 |
| Soybean flour | 25.0 |
| Blackstrap molasses | 5.0 |
| $CaCO_3$ | 4.0 |
| $Fe(SO_4)\cdot(NH_4)_2SO_4\cdot 6H_2O$ | 0.6 |
| Tap water | q.s. 1 liter |

Different amino acids were added to study their effects on the A54145 nuclei and acyl side chains produced. Table IV summarizes the results of these studies.

TABLE IV

EFFECT OF AMINO ACID ENRICHMENT ON BIOSYNTHESIS OF A54145 NUCLEI AND ACYL CHAINS IN SHAKEN FLASKS

| Amino Acid | Level (M) | Total Antibiotic (%) | Nuclei[a] | | | | Acyl Chains[a,b] | | |
|---|---|---|---|---|---|---|---|---|---|
| | | | A | B | C | F | $iC_{10}$ | $nC_{10}$ | $aC_{11}$ |
| — | — | 100[c] | 50 | 39 | 1 | 10 | 65 | 18 | 17 |
| L-Val | .03 | 32 | 32 | 20 | 2 | 54 | 98 | 0 | 2 |
| L-Leu | .02 | 56 | 42 | 40 | 2 | 16 | 76 | 7 | 17 |
| L-Ile | .04 | 73 | 48 | 47 | 2 | 0 | 16 | 18 | 66 |
| L-Glu | .02 | 85 | 49 | 39 | 1 | 11 | 63 | 20 | 16 |
| L-Asp | .005 | 134 | 56 | 34 | 1 | 10 | 64 | 19 | 17 |
| L-Tyr | .02 | 59 | 12 | 76 | 1 | 11 | 67 | 18 | 15 |

[a]Percent of total produced
[b]$iC_{10}$ = 8-methylnonanoyl
$nC_{10}$ = n-decanoyl
$aC_{11}$ = 8-methyldecanoyl
[c]550 mcg/mL Table V summarizes the results of a similar study of the effect L-tyrosine has on A54145 production. This study was made in a 115-liter fermentation run.

TABLE V

EFFECT OF L-TYROSINE ENRICHMENT ON BIOSYNTHESIS OF A54145 NUCLEI IN A BIOREACTOR (115 L OF MEDIUM)

| Amino Acid | Level (M) | Total Antibiotic (%) | Nuclei[a] | | | | Acyl Chains[a,b] | | |
|---|---|---|---|---|---|---|---|---|---|
| | | | A | B | C | F | $iC_{10}$ | $nC_{10}$ | $aC_{11}$ |
| — | — | 100[c] | 19 | 78 | 1 | 2 | 19 | 74 | 7 |
| L-Tyr | 0.01 | 102 | 10 | 87 | 1 | 1 | 28 | 67 | 5 |

[a]Percent of total produced
[b]$iC_{10}$ = 8-methylnonanoyl
$nC_{10}$ = n-decanoyl
$aC_{11}$ = 8-methyldecanoyl
[c]3200 mcg/mL Comparing the results in Tables IV and V shows that the scale of the fermentation affects the amount of a) total antibiotic produced, b) nuclei produced and c) acyl side chains produced. Adding L-tyrosine decreased total antibiotic production in the shaken-flask fermentation, but did not adversely affect production in the tank fermentation. The unsupplemented shaken-flask fermentation produced more A nucleus and more $iC_{10}$ side chain product, whereas the unsupplemented tank fermentation produced more B nucleus and more $nC_{10}$ side chain. L-tyrosine increased the percentage of B-nucleus produced in both shaken flasks and tanks, but the effect was more pronounced in flasks.

Adding L-valine or L-leucine increased the percentage of F nucleus produced and the percentage of $iC_{10}$ side chain product. This effect was more pronounced with L-valine.

Adding L-isoleucine increased the percentage of both B nucleus and $aC_{11}$ side chain produced.

PREPARATION 17

An A54145 fermentation was carried out as described in Preparation 3 except that the following production medium was used:

| Ingredient | Amount (g/L) |
|---|---|
| Soybean flour | 30.0 |
| Blackstrap molasses | 5.0 |
| Glucose | 3.0 |
| $Fe(SO_4)\cdot(NH_4)_2SO_4\cdot 6H_2O$ | 0.6 |
| Deionized water | q.s. 1 liter |

Antifoam agents were added, and the pH was adjusted from ~6.2 to ~7.2 with 5N NaOH.

Beginning about 23 hours after the fermentation was initiated, glucose was fed to the fermentation at a rate of approximately 6.5 g/L/day. Beginning at about 25 hours after the fermentation was initiated, a sterile solution consisting of decanoic acid and oleic acid (1:1, v/v) was fed to the fermentation at a rate of approximately 6.0 mL/L/day.

At about 117 hours after the fermentation was initiated, a feeding of enzymatic soy digest was initiated and continued at a rate of about 3.0 g/L/day.

The yield of A54145 from the fermentation after about 280 hours was 3969 mcg/mL. This yield is substantially greater than the yield of about 500 mcg/mL ordinarily obtained using similar conditions, but without the glucose, enzymatic soy digest and decanoic acid feeds used in this fermentation.

PREPARATION 18

Another series of fermentations was carried out using the procedures of Preparation 15 with Medium C, but adding different $C_4$-$C_{18}$-alkanoic acids and esters to enhance A54145 production. The results of these studies are shown in Table VI.

TABLE VI
EFFECT OF LIPID PRECURSORS ON BIOSYNTHESIS OF A54145 SIDE CHAINS IN A 165-L BIOREACTOR

| Precursor | $RQ^a$ Calcd.$^d$ | $RQ^a$ Found$^e$ | Total A54145 (%) | Known Side Chains Percent of Total $iC_{10}$ | $nC_{10}$ | $aC_{11}$ | New Analogs$^{b,c}$ $C_6A$ | $C_6B$ | $C_8A$ | $C_8B$ | $C_9A$ | $C_9B$ |
|---|---|---|---|---|---|---|---|---|---|---|---|---|
| None | 1.0 | 1.0 | 100$^f$ | 76 | 14 | 10 | | | | | | |
| Acetate | 1.0 | 1.0 | 104 | 73 | 15 | 11 | | | | | | |
| Propionate | 0.88 | 0.96 | 28 | 69 | 22 | 8 | | | | | | |
| Butyrate | 0.8 | 0.93 | 49 | 28 | 58 | 15 | | | | | | |
| Hexanoate | 0.75 | 0.83 | 56 | 2 | 2 | — | 67 | 29 | | | | |
| Caprylate | 0.73 | 0.8 | 84 | 17 | 9 | 5 | | | 33 | 36 | | |
| Nonanoate | 0.72 | 0.85 | 95 | — | — | — | | | | | 75 | 25 |
| Caprate | 0.71 | 0.86 | 184 | 17 | 91 | 2 | | | | | | |
| Undecanoate | 0.76 | 0.9 | 136 | 11 | 3 | 26 | | | | | 17 | 16 |
| Undecylenate | 0.71 | 0.87 | 153 | 27 | 56 | 2 | | | | | | |
| Laurate | 0.71 | 0.9 | 154 | 43 | 54 | 3 | | | | | | |
| Tridecanoate$^g$ | 0.7 | 0.76 | 64 | 40 | 19 | 5 | | | | | 12 | 28 |
| Myristate | 0.7 | 0.81 | 207 | 10 | 85 | 5 | | | | | | |
| Oleate | 0.7 | 0.9 | 142 | 49 | 48 | 3 | | | | | | |
| Decyl Alcohol | 0.67 | 0.86 | 157 | 22 | 75 | 3 | | | | | | |

$^a$Respiration Quotient
$^b$Abbreviations as follows: "$C_6A$" = A nucleus with a $C_6$ side chain
$^c$Undecanoate and tridecanoate precursors each produced two additional unknown factors [amounts: 13 and 14% (undecanoate) and 7 and 8% (tridecanoate)]
$^d$For metabolism as sole carbon source
$^e$Represents glucose metabolism or co-metabolism with glucose
$^f$1100 mcg/mL
$^g$In 50% methyl oleate

PREPARATION 19

Preparation of $N_{Lys}$-(t-BOC)$N_{Trp}$-(n-Undecanoyl)-A54145A Nucleus and $N_{Trp}$-(n-Undecanoyl)-A54145A Nucleus

A. n-Undecanoyl Trichlorophenyl Ester

Undecanoic acid (7.5 g) was added to a solution of 2, 4, 5-trichlorophenol (8.6 g) in tetrahydrofuran (THF) (175 mL, anhyd.). This mixture was chilled in an ice bath and stirred under nitrogen for 10 minutes. The reaction mixture was removed from the ice bath, and N,N-dicyclohexylcarbodiimide (DCC) (9.0 g) was added.

The reaction mixture was stirred overnight under nitrogen at room temperature and then was concentrated to a volume of about 100 mL under vacuum. The concentrate was filtered to remove precipitated material, and the filtrate was evaporated to dryness.

The residue obtained was dissolved in diethyl ether and hexane. This solution was concentrated under vacuum and filtered to remove the red-pink precipitate which formed. The filtrate was evaporated under vacuum. The white precipitate which formed was collected by filtration and dried to give 5.27 g of n-undecanoyl "active ester".

B. Acylation of $N_{Lys}$-(t-BOC)-A54145A Nucleus $N_{Lys}$-(t-BOC-)-A54145A nucleus (500 mg) was added to anhydrous DMF (15 mL) in a 50-mL round bottom flask. After the solution was purged with nitrogen, the undecanoyl "active" ester (300 mg) and hydroxybenzotriazole (HBT) (8 mg) were added. The reaction mixture was stirred under nitrogen at room temperature for 21 hours and then concentrated under vacuum to a low volume (about 1/10th). Diethyl ether (30 mL) was added, and the precipitate which formed was separated by sonicating the suspension and filtering. The precipitate was washed twice with diethyl ether (30 mL each) and dried under vacuum to give the 425 mg of $N_{Lys}$-(t-BOC)-$N_{Trp}$-(n-undecanoyl)-A54145A nucleus.

C. Deblocking

The t-BOC derivative obtained in Section B was dissolved in trifluoroacetic acid (5 mL) containing anisole (0.5 mL) and stirred at room temperature for one hour under nitrogen. The solution was concentrated under vacuum to a low volume. A precipitate was formed by adding $CH_2Cl_2$/diethyl ether (2:1, 30 mL). The precipitate was separated by filtration and washed twice with $CH_2Cl_2$/diethyl ether (2:1, 30 mL each) and dried. The residue was dissolved in water (10 mL). The pH of the solution (1.72) was adjusted to 6.2 with pyridine, and the solution was lyophilized to give 645.5 mg of product.

D. Purification by Preparative HPLC

The product obtained in Section C was purified by preparative HPLC, using the following conditions:
Column: 1-×12-in. Zorbax ODS (Dupont, 12μ)
Detection: UV at 280 nm
Flow Rate: 9 mL/min The material, dissolved in solvent 1 (5 mL), was injected onto the column. The column was eluted at a flow rate of 9 mL/min, collecting 18-mL fractions, as follows:

| Solvent | Fractions |
|---|---|
| 1 | 1–10 |
| 3g | 11–63 |
| 4 | 64–80 |

Fractions were monitored by analytical HPLC, using the following conditions:
Column: 4.6-×250-mm Zorbax ODS (Dupont, 5μ)
Detection: UV at 223 nm
Flow Rate: 2 mL/min Solvent: $CH_3CN:MeOH:0.04$ M aq. $NH_4OAc$ (25:12.5:62.5)

Fractions containing the product were combined, concentrated and lyophilized to give 241 mg of $N_{Trp}$-(n-undecanoyl)-A54145A nucleus.

FABMS (M+1): 1658

UV (EtOH): 280 nm ($\epsilon$ 4,752) and 220 nm ($\epsilon$ 34,413).

EXAMPLE 1

Preparing A54145A Nucleus

A. Fermenting *Actinoplanes utahensis*

A stock culture of *Actinoplanes utahensis* NRRL 12052 is prepared and maintained under liquid nitrogen as described in U.S. Pat. No. 4,524,135 (cols. 22–23) or on slants, using the following medium:

| MEDIUM A | |
|---|---|
| Ingredient | Amount |
| Oatmeal | 20.0 g |
| Sucrose | 20.0 g |
| Yeast (debittered dried brewer's) | 2.5 g |
| Corn distillers dried solubles* | 5.0 g |
| $K_2HPO_4$ | 1.0 g |
| Czapek's mineral stock** | 5.0 mL |
| Deionized water | q.s. to 1 liter |

*Nadrisol, National Distillers Products Co., 99 Park Ave., New York, NY
**Czapek's mineral stock has the following composition:

| Ingredient | Amount |
|---|---|
| $FeSO_4.7H_2O$ (dissolved in 2 mL conc HCl) | 2 g |
| KCl | 100 g |
| $MgSO_4.7H_2O$ | 100 g |
| Deionized water | q.s. to 1 liter |

For agar slants, 20.0 g agar is added to Medium A. Slants are incubated at 30° for about 8 to 10 days.

Liquid nitrogen suspension (1 mL) is used to inoculate 200 mL of a vegetative medium (Medium A). The inoculated vegetative medium is incubated in a 1-L wide-mouth Erlenmeyer flask at 30° C. for about 76 hours on a shaker rotating through an arc two inches in diameter at 250 RPM.

The incubated vegetative medium (500 mL) is used to inoculate 10 liters of sterile production medium having the following composition:

| MEDIUM B | |
|---|---|
| Ingredient | Amount (g/L) |
| Peanut meal | 10.0 |
| Soluble meat peptone | 5.0 |
| Sucrose | 20.0 |
| $KH_2PO_4$ | 0.5 |
| $K_2HPO_4$ | 1.2 |
| $MgSO_4.7H_2O$ | 0.25 |
| Tap water | q.s. to 1 liter |
| Post-sterilization pH is ~6.9. | |

The inoculated production medium is allowed to ferment in a 14-liter fermentation tank at a temperature of about 30° C. for about 68 hours. The fermentation medium is stirred with conventional agitators at about 600 RPM and aerated with sterile air to maintain the dissolved oxygen level at or above 30% of air saturation at atmospheric pressure.

B. Deacylating A54145A

A fermentation of *A. utahensis* is carried out as described in Section A. After incubating the production medium for about 68 hours, A54145A (50 g) in water (300 mL) is added. The pH of the medium is adjusted to 7.2 with NaOH.

The fermentation is allowed to continue at 30° C., stirring at 600 RPM to maintain the dissolved oxygen level at 30% or above, until deacylation is complete. Deacylation is measured by disappearance of activity vs. *Micrococcus luteus* (about 22 hrs).

C. Isolating A54145A and A54145F Nuclei

Whole fermentation broth (10 liters), obtained as described in Section B, was vacuum filtered with Hyflo SuperCel (2L). The mycelial cake was washed with water (3L) and then discarded. The original filtrate (9.5L) and the mycelial wash (3L) were combined. This solution was adjusted to pH 3.5 with HCl, mixed with 1.4 liters of HP-20 resin (Diaion High Porous Polymer, HP-Series, Mitsubishi Chemical Industries Limited, Tokyo, Japan), stirred for 1 hr and placed in a 6.5-×75-cm column. The first effluent (13L) and a water wash (adjusted to pH 2 with HOAc) were discarded. The column was then eluted with $CH_3CN:H_2O$ (1:9) (5L). This eluate was concentrated under vacuum and lyophilized to give 14.25 g of crude nucleus.

The crude nucleus was subjected to preparative HPLC using the following system:

Column: 2"×60-cm reverse-phase silica gel (Quantum LP-1/$C_{18}$)

Detection: UV at 280 nm

The crude nucleus (14 g) was dissolved in Solvent No. 1 and injected onto the column. The column was eluted at a flow rate of 12 mL/min. as follows:

| Solvent No. | Fractions[a] |
|---|---|
| 1 | 1–16 |
| 2a | 17–269 |
| 4 | 270–330 |

[a]Fraction volume: 24 mL

Fractions containing A54145F nucleus (fractions 84–106) were combined, concentrated and lyophilized to give 1.95 g of impure A54145F nucleus, and fractions containing A54145A nucleus (fractions 150–250) were combined, concentrated and lyophilized to give 4.8 g of impure A54145A nucleus.

D. Purifying A54145A Nucleus

Impure A54145A nucleus (1.9 g), obtained as described in Section C, was purified by HPLC as in Section C, but using two 1"×12" silica gel (Zorbax ODS, 12μ) columns in series.

The nucleus was applied to the column in solvent 1. The column was eluted at a flow rate of 8 mL/min as follows:

| Solvent No. | Fractions[a] |
|---|---|
| 1 | 1–25 |
| 2 | 26–93 |
| 2a | 94–177 |
| 4 | 178–200 |

[a]Fraction volume: 16 mL

Fractions containing A54145A nucleus (fractions 111–117) were combined, concentrated and lyophilized to give 457 mg of A54145A nucleus.

EXAMPLE 2

Preparing A54145B Nucleus

A. Deacylating A54145

A culture of *Actinoplanes utahensis* NRRL 12052, prepared in medium A, incubated for eight days at 30° C. and stored at 4° C., was used to inoculate 50 mL of a vegetative medium (medium A) in a 250-mL Erlenmeyer flask. The vegetative medium was incubated at 30° C. on a rotary shaker at 250 RPM for 48 hours.

Incubated vegetative medium (5 mL) was used to inoculate 100 mL of sterile production medium (medium B) in a 500-mL Erlenmeyer flask. The production medium was incubated at 30° C. on a rotary shaker at 250 RPM for 120 hours.

Semi-pure antibiotic A54145B (100 mg) in water (2 mL) was added to the production flask. The culture was then incubated at 30° C. on rotary shakers at 250 RPM for another 20 hours to achieve complete deacylation.

B. Isolating A54145B Nucleus

Whole fermentation broth (100 mL at pH 6.8), prepared as described in Section A, was vacuum filtered. The mycelial cake was washed with water (20 mL), and the water wash was combined with the filtrate. This solution was adjusted to pH 4.5 with HCl and added to an HP-20 resin column (38 mL). The initial efluent (112 mL) and a water wash (adjusted to pH 3 with HCl, 111 mL) were discarded. The column was then eluted with $CH_3CN:H_2O$ (3:1, 100 mL). This eluent was concentrated under vacuum and lyophilized to give 169 mg of crude A54145B nucleus.

C Purifying A54145B Nucleus

The crude nucleus (169 mg) was dissolved in solvent No. 1 and injected on a preparative HPLC column, using the following system:
Column: Two 9.4-×250-mm Zorbax ODS (5μ) columns in series
Detection: UV at 280 nm
Flow Rate: 2 mL/min
The column was eluted as follows:

| Solvent No. | Fractions[a] |
| --- | --- |
| 1 | 1-20 |
| 2b | 21-153 |
| 2d | 154-168 |
| 3h | 169-186 |
| 4 | 187-200 |

[a]Fraction volume: 4 mL

Fractions containing A54145B nucleus (#122-150) were combined, concentrated and lyophilized to give 39 mg of A54145B nucleus.

EXAMPLE 3

Preparing A54145C Nucleus

A. Deacylating A54145C

A production culture of *Actinoplanes utahensis* NRRL 12052 was obtained as described in Example 2, but using two 50-mL Erlenmeyer flasks each containing 10 mL of medium. Impure A54145C (10 mg) in water (1 mL) was added to each flask.

B. Isolating A54145C Nucleus

The culture was harvested and worked up as described in Example 2, using a 3-mL water wash and combining it with the filtrate. The wash/filtrate solution was adjusted to pH 4.5 with HCl and chromatographed over HP-20 resin (7 mL). The initial efluent (14 mL) and a water wash (adjusted to pH 3 with HCl, 10 mL) were discarded. The column was then eluted with $CH_3CN:H_2O$ (3:1, 12 mL). This eluate was concentrated and lyophilized to give 35.6 mg of crude A54145C nucleus.

C. Purifying A54145C Nucleus

The crude nucleus (35 mg) dissolved in solvent No. 1 (3 mL) and injected onto a preparative HPLC column, using the system of Example 2.

The column was eluted as follows:

| Solvent No. | Fractions[a] |
| --- | --- |
| 1 | 1-22 |
| 2 | 23-66 |
| 2c | 67-85 |
| 2e | 86-105 |
| 2h | 106-124 |
| 4 | 125-136 |

[a]Fraction volume: 6 mL

Fractions containing A54145C nucleus (#75-81) were combined, concentrated and lyophilized to give 5.5 mg of A54145C nucleus.

EXAMPLE 4

Preparing $N_{Lys}$-(t-BOC)-A54145

Crude A54145 (25 g) was dissolved in water (200 mL adjusted to pH 3.7). This solution was adjusted to pH 9.1 with 5N NaOH and stirred at ambient temperature. Di-tert-butyl dicarbonate (32 mL) and tert-butanol (50 mL) were added, and the solution was stirred for 4½ hours. The solution was then lyophilized. The residue thus obtained was dissolved in water (400 mL) and extracted 3 times with equal volumes of dichloromethane. The aqueous phase was then concentrated and lyophilized to give 39 g of $N_{Lys}$-(t-BOC)A-54145.

The reaction was monitored by analytical HPLC using the following system:
Column: 4.6-×250-mm Eorbax ODS ($C_{18}$ 5μ)
Detection: UV at 289 and 223 nm
Flow Rate: 2 mL/min
Solvent: $CH_3CN:MeOH:0.04$ M aq.$NH_4OAc$ (25:12.5:62.5)

This reaction was repeated except that the pH was maintained at 8.5-9.0 with NaOH and only 7 mL of di-tert-butyl dicarbonate was added. Under these conditions, the reaction took place in only 80 minutes.

EXAMPLE 5

Preparing $N_{Lys}$-(t-BOC)-A54145 Nucleus

The procedure of Example 1, Section A, was repeated except that the vegetative medium had the following composition:

| MEDIUM C | |
| --- | --- |
| Ingredient | Amount (g/L) |
| Sucrose | 20 |
| Soybean flour | 10 |
| $K_2HPO_4$ | 1.2 |
| $KH_2PO_4$ | 0.5 |
| $MgSO_4.7_2O$ | 0.25 |
| Defoamer* | 0.3 |

-continued

MEDIUM C

| Ingredient | Amount (g/L) |
| --- | --- |
| Tap water | q.s. to 1 L |
| Adjust pH to 6.8 if necessary | |

*Sag 471 (Union Carbide)

The first-stage medium had a volume of 800 mL (400 mL/2-L flask) and was incubated at 30° C. on a rotary shaker for 72 hr.

The second stage medium (Medium C) had a volume of 950L. The fermentation was carried out in a 350-gal. fermentor at 30° C., stirring at 155 RPM with an air flow of 28 cfm for 72 hours.

The second-stage medium was used to inoculate 810L of production medium (Medium B) in a 350-gal. fermentor. This fermentation was carried out at 30° C, stirring at 130 RPM with an air flow of 10 cfm for 43 hours.

A portion of this production medium (15L) was transferred to a 68-L fermentor and $N_{Lys}$-(t-BOC)-A54145 (prepared from 50 g of A54145 as described in Example 4 and dissolved in water) was added. The fermentation was continued at 30° C. until deacylation was complete as determined by HPLC to give $N_{Lys}$-(t-BOC)-A54145 nucleus.

EXAMPLE 6

Purifying $N_{Lys}$-(t-BOC)-A54145 Nucleus

Whole fermentation broth (18L), obtained as described in Example 5, was vacuum filtered with 2-3L of filter aid (Hyflo Super-Cel). The mycelial cake was rinsed with water (2L) and filtered. The water wash was combined with the original filtrate (18L). The mycelial cake was extracted with methanol (4L) and again filtered. The methanol extract was concentrated to remove the methanol, and the aqueous solution remaining was lyophilized. The lyophilized material was reconstituted in water (500 mL) and combined with the filtrate and water wash to give a total volume of 20.5L.

This solution was adjusted to pH 4.7 with HCl mixed with HP-20 resin (2.4L), stirred for 2 hours and then placed in a 2"×60" column. The initial effluent (22L) and the initial water wash (adjusted to pH 3.5 with HOAc, 14.5L) were discarded. The column was then eluted with $CH_3CN/H_2O$ in the following ratios and amounts: 5:95 (4L); 1:9 (4L); 15:85 (2L); 3:7 (8L). The 3:7 eluate was concentrated and lyophilized to give 23.0 g of purified $N_{Lys}$-(t-BOC)-A54145 nucleus.

EXAMPLE 7

Separation of $N_{Lys}$-(t-BOC)-A54145A Nucleus and $N_{Lys}$-(t-BOC)-A54145F Nucleus $N_{Lys}$-(t-BOC)-A54145 nucleus (23 g), prepared as described in Example 6, was subjected to preparative HPLC, using a Chromatospac 100 silica-gel column (4L, Quantum LP-1/C18). The material was dissolved in Solvent 1 (200 mL) and added to the column. Elution was monitored at 280 nm. The column was eluted at a flow rate of 60 mL/min as follows:

| Solvent No. | Fractions[a] |
| --- | --- |
| 1 | 1-5 |
| 3i | 6-70 |
| 4 | 71-73 |

[a]Fraction volume: 480 mL

Fractions were combined based on analytical HPLC, using the following system:
Column 4.6-×250-mm Zorbax ODS (5μ)
Detection: UV at 223 nm
Solvent $CH_3CN$/MeOH/0.04 M aq. $NH_4OAc$ (12.5:5:82.5)
Flow rate: 2 mL/min From this column, fractions 28-31 gave 1.8 g of $N_{Lys}$-(t-BOC)-A54145F nucleus, and fractions 39-42 gave 2.6 g of $N_{Lys}$-(t-BOC)-A54145A nucleus.

EXAMPLE 8

A54145F Nucleus $N_{Lys}$-(t-BOC)-A54145F nucleus is deblocked using standard procedures to give A54145F nucleus.

EXAMPLE 9

Separation of $N_{Lys}$-(t-BOC)-A54145B Nucleus $N_{Lys}$-(t-BOC)-A54145 nucleus was prepared as described in Example 6, using 10L of production medium in Step A and 120 g of $N_{Lys}$-(t-BOC)-A54145 in Step B to give 79.65 g of $N_{Lys}$-(t-BOC)-A54145 nucleus.

This nucleus was treated as in Example 7 to separate fractions containing different nuclei. $N_{Lys}$-(t-BOC)-A54145B nucleus was eluted with solvent No. 2c to give 21.1 g of enriched material.

This material was purified by 2 sets of two 1"×12" Zorbax ODS 12μ columns. The first set of columns was eluted with pyridine/HOAc/$H_2O$/$CH_3CN$ (1:1:49:49) to give 2.6 g of product. This product was purified over the second set of columns, eluting with solvent 2e, to give 0.38 g of $N_{Lys}$-(t-BOC)-A54145B nucleus.

We claim:

1. A compound of the formula:

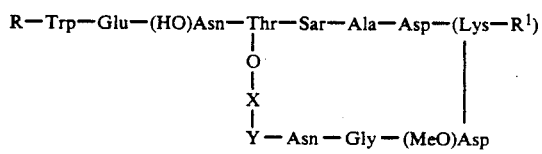

wherein:

R-Trp represents a group of formula:

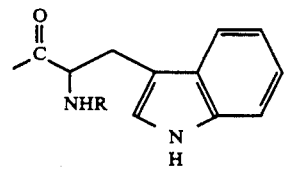

R is selected from the group consisting of hydrogen, an amino-protecting group, 8-methylnonanoyl, 8-methyldecanoyl and n-decanoyl;
(Lys-$R^1$) represents —$NH(CH_2)_4CH(NHR^1)CO$—;
$R^1$ is hydrogen or an amino-protecting group;
X is Ile or Val; and
Y is Glu or 3-MG;
provided that $R^1$ cannot be hydrogen when R is 8-methylnonanoyl, 8-methyldecanoyl or n-decanoyl; or a pharmaceutically-acceptable salt thereof.

2. A compound of claim 1 wherein R is hydrogen.

3. A compound of claim 2 wherein $R^1$ is hydrogen.

4. A compound of claim 1 wherein X is Ile and Y is Glu.

5. A compound of claim 1 wherein X is Ile and Y is 3-MG.

6. A compound of claim 1 wherein X is Val and Y is Glu.

7. A compound of claim 1 wherein X is Val and Y is 3-MG.

8. The compound of claim 4 wherein R and $R^1$ are hydrogen.

9. The compound of claim 5 wherein R and $R^1$ are hydrogen.

10. The compound of claim 6 wherein R and $R^1$ are hydrogen.

11. The compound of claim 7 wherein R and $R^1$ are hydrogen.

12. A compound of claim 1 wherein R is an amino-protecting group.

13. A compound of claim 1 wherein $R^1$ is an amino-protecting group.

14. A compound of claim 12 wherein X is Ile and Y is Glu.

15. A compound of claim 12 wherein X is Ile and Y is 3-MG.

16. A compound of claim 12 wherein X is Val and Y is Glu.

17. A compound of claim 12 wherein X is Val and Y is 3-MG.

18. A compound of claim 1 where R is selected from 8-methylnonanoyl, 8-methyldecanoyl, and n-decanoyl.

* * * * *